United States Patent
Ishikawa et al.

(10) Patent No.: US 7,960,175 B2
(45) Date of Patent: Jun. 14, 2011

(54) PROCESS FOR PRODUCING HUMAN-ORIGIN IMMUNOCOMPETENT CELL

(75) Inventors: Fumihiko Ishikawa, Fukuoka (JP); Mine Harada, Fukuoka (JP); Masaki Yasukawa, Matsuyama (JP)

(73) Assignee: Kyushu University, National University Corporation, Fukuoka-shi (JP)

( * ) Notice: Subject to any disclaimer, the term of this patent is extended or adjusted under 35 U.S.C. 154(b) by 51 days.

(21) Appl. No.: 10/560,829

(22) PCT Filed: Jun. 16, 2004

(86) PCT No.: PCT/JP2004/008784
§ 371 (c)(1),
(2), (4) Date: Mar. 7, 2006

(87) PCT Pub. No.: WO2004/110139
PCT Pub. Date: Dec. 23, 2004

(65) Prior Publication Data
US 2006/0161996 A1    Jul. 20, 2006

(30) Foreign Application Priority Data
Jun. 16, 2003   (JP) .................................. 2003-171240

(51) Int. Cl.
*C12N 5/071*   (2010.01)
(52) U.S. Cl. .................. 435/372; 435/372.2; 435/372.3; 435/373
(58) Field of Classification Search .................. None
See application file for complete search history.

(56) References Cited

U.S. PATENT DOCUMENTS

| | | | |
|---|---|---|---|
| 5,789,560 A | 8/1998 | Etzbach et al. | |
| 2002/0199213 A1 | 12/2002 | Tomizuka et al. | |
| 2007/0067854 A1 | 3/2007 | Habu et al. | |

FOREIGN PATENT DOCUMENTS

| | | |
|---|---|---|
| EP | 1338198 A1 | 8/2003 |
| WO | WO-92/03918 A1 | 3/1992 |
| WO | WO 01/87058 A1 | 11/2001 |
| WO | WO-02/43478 A2 | 6/2002 |
| WO | WO-0243477 A1 | 6/2002 |
| WO | WO 02/065992 A2 | 8/2002 |
| WO | WO 03/002140 A1 | 1/2003 |

OTHER PUBLICATIONS

Ishikawa et al. Exp. Hematol. 30(5):488-494; May 2002.*
Ishikawa et al. Exp. I-Iernatol. 30(5):488-494; May 2002.*
Olive et al. Imm. Cell Biol. 76:520-525; 1998.*
JAX Mice Database Strain NOD.Cg-Prkdcscid II2rgtm1Wjl/SzJ; pp. 1-2; The Jackson Laboratory (no date).*
Ishikawa et al., Experimental Hematology, May 2002, vol. 30, No. 5, pp. 488-494.
Ishikawa, F. et al., Annals of the New York Academy of Sciences, May 2003, vol. 996, pp. 174-185.
Fraser et al., Experimental Hematology, Sep. 2002, vol. 30, No. 9, pp. 1070-1078.
Ito et al., Blood, Nov. 2002, vol. 100, No. 9, pp. 3175-3182.
Japanese Application No. 2005-507024; Notice of Reasons for Rejection with English translation, Nov. 24, 2009, 6 pages.

* cited by examiner

*Primary Examiner* — James (Doug) Schultz
(74) *Attorney, Agent, or Firm* — Birch, Stewart, Kolasch & Birch, LLP.

(57) ABSTRACT

It is an object of the present invention to provide an immunodeficient animal capable of generating human-derived lymphoid cells, a human-derived lymphoid cell, and a method for producing a human antigen-specific antibody.

The means for solving the aforementioned object is: an immature immunodeficient mammal into which human-derived hematopoietic precursor cells have been transplanted, and which is able to generate said human-derived hematopoietic cells or immunocompetent cells; and a method for producing a human-derived antibody, which is characterized in that it comprises recovering immunocompetent cells from the above-described mammal, culturing the immunocompetent cells, and collecting a human-derived antibody from the obtained culture product.

13 Claims, 13 Drawing Sheets

PROCESS FOR PRODUCING HUMAN-ORIGIN IMMUNOCOMPETENT CELL

TECHNICAL FIELD

The present invention relates to a technique used for the in vivo growth of various cells essential for immune response, such as human lymphoid cells or antigen-presenting cells, and the reconstruction of a human immune system.

BACKGROUND ART

It is important for studies regarding human stem cells to conduct measurement in vivo. Thus, such studies are carried out based on xenogeneic transplantation using immunodeficient rodents or sheep fetuses (Flake, A. W. et al., 1986. Science 233: 776-778.). In 1988, McCune et al. have reported Scid-hu assay (Science 241: 1632-1639 (1988)). This assay constituted a first case where human cells were detected in a CB17/SCID mouse. Thereafter, as recipients into which human hematopoietic cells are to be transplanted, many types of immunodeficient mice have been used. Examples of such immunodeficient mice may include NOD/SCID (Pflumio, F. et al., 1996. Blood 88:3731-3740.), NOD/RAG-1$^{null}$ (Shultz, L. D. et al., 2000. Journal of Immunology 164:2496-2507.), beige/nude/scid (Dao, M. A., and J. A. Nolta. 1998. International Journal of Molecular Medicine 1:257-264.), and NOD/SCID/β2M$^{null}$ (Kollet, O. et al., 2000. Blood 95: 3102-3105.).

However, a majority of mice used as recipients for transplantation of stem cells in xenogeneic animals are adult mice with an age of 8 to 12 weeks old. In addition, in the case of using common SCID adult mice, in order to maintain a graft for a long period of time, administration of extrinsic cytokine is necessary. Moreover, it is difficult to allow T cells to differentiate from precursor cells (Ito, M. et al., 2002. Blood 100:3175-3182.).

DISCLOSURE OF THE INVENTION

It is an object of the present invention to construct a human immune system in a xenogeneic animal host, so that an immune reaction can be allowed to take place naturally or artificially, thereby generating necessary human immunocytes, and in particular, antigen-specific T cells, B cells, immunoglobulins, cytokines, or the like.

As a result of intensive studies directed towards solving the aforementioned object, the present inventors have found that the aforementioned object can be achieved by transplanting hematopoietic precursor cells or mature hematopoietic cells into an immunodeficient animal, thereby completing the present invention.

That is to say, the present invention includes the following features of the invention:

(1) The present invention relates to an immature (including the stages ranging from a fetus and a newborn, up to an individual with a reproductive age) immunodeficient mammal (excluding human), into which human-derived hematopoietic precursor cells or mature hematopoietic cells have been transplanted, and which is able to generate immunocompetent cells derived from the above-described human and/or physiologically active substances derived from the above-described immunocompetent cells. In addition, the present invention relates to an immunodeficient mammal obtained as a result of the breeding of the above-described immature immunodeficient mammal (excluding human), or a progeny thereof.

Examples of the above-described immature immunodeficient mammal may include a newborn immunodeficient mammal and a fetal immunodeficient mammal.

In addition, examples of the above-described hematopoietic precursor cells may include cells, which are derived from bone marrow, cord blood, G-CSF-mobilized peripheral blood, ES cell-derived mesodermal cells, or peripheral blood. Specific examples of such cells are CD34 positive cells (e.g., CD34$^+$ cells, CD133$^+$ cells, SP cells, CD34$^+$CD38$^-$ cells, c-kit$^+$ cells, or those exhibiting CD3$^-$, CD4$^-$, CD8$^-$ and CD34$^+$). The above-described immunocompetent cells are at least one selected from the group consisting of B cells, T cells, dendritic cells, NK cells, and NKT cells. Such immunocompetent cells can be collected from the peripheral blood of a recipient without sacrificing the recipient. When a large number of cells or physiologically active substances derived from the aforementioned immunocompetent cells (for example, an immunoglobulin, a cytokine, etc.) are purified, bone marrow, spleen, thymus, lymph node, or the like can be used as a source of cells. The above-described immunodeficient mammal is preferably an immunodeficient mouse. The above immunoglobulin includes all isotypes such as IgG, IgM, IgA, IgD, and IgE.

(2) The present invention also relates to a method for producing a mammal capable of generating immunocompetent cells derived from a human and/or physiologically active substances derived from the above-described immunocompetent cells, or a progeny thereof, which is characterized in that it comprises transplantation of human-derived hematopoietic precursor cells or mature hematopoietic cells into an immature immunodeficient mammal (excluding human). Examples of such an immature immunodeficient mammal may include a newborn immunodeficient mammal and a fetal immunodeficient mammal. In addition, examples of the above-described hematopoietic precursor cells may include cells, which are derived from bone marrow, cord blood, G-CSF-mobilized peripheral blood, ES cell-derived mesodermal lineage cells, or peripheral blood. Specific examples of such cells are CD34 positive cells (e.g., CD34$^+$ cells, CD133$^+$ cells, SP cells, CD34$^+$CD38$^-$ cells, c-kit$^+$ cells, or those exhibiting CD3$^-$, CD4$^-$, CD8$^-$ and CD34$^+$). The above-described immunocompetent cells are at least one selected from the group consisting of B cells, T cells, dendritic cells, NK cells, and NKT cells. Examples of the above-described physiologically active substance may include a cytokine and/or an immunoglobulin. The above immunoglobulin includes all isotypes such as IgG, IgM, IgA, IgD, and IgE. The above-described immunodeficient mammal is preferably an immunodeficient mouse.

(3) In addition, the present invention also relates to a method for producing a human-derived antibody, which is characterized in that it comprises recovering immunocompetent cells from the above-described immunodeficient mammal or a progeny thereof, culturing the above-described immunocompetent cells in the presence of an antigen or a suitable stimulator, and collecting the above-described human-derived antibody from the obtained culture product. The above-described immunocompetent cells are at least one selected from the group consisting of B cells, T cells, dendritic cells, NK cells, and NKT cells.

(4) Moreover, the present invention also relates to a method for producing the above-described human-derived antibody, which is characterized in that it comprises immunizing the above-described immunodeficient mammal or a progeny thereof with an antigen or a stimulator, and collecting the above-described human-derived antibody from the immunized mammal. Such an antibody is collected from blood plasma or serum, for example.

(5) Furthermore, the present invention relates to a disease-model mammal, which is produced by administering to the above-described immunodeficient mammal or a progeny thereof, any one selected from the group consisting of bacteria, viruses, tumor cells, and tumor antigen peptides, or a progeny thereof. An example of the above-described disease is an infectious disease.

(6) The present invention relates to a method for screening for an immune-related pharmaceutical, which is characterized in that it comprises administering a test substance to the above-described immunodeficient mammal or a progeny thereof, or to the above-described animal with an infectious disease or a progeny thereof, and evaluating the effectiveness of the test substance. Such an immune-related pharmaceutical includes a vaccine, an antiviral agent, and an antibiotic. Moreover, the above method is also useful in confirming immune response to the human antibody of the present invention and the safety thereof against allergy (in particular, at a preclinical test stage).

(7) The present invention relates to a method for producing immunocompetent cells, which is characterized in that it comprises recovering the above-described immunocompetent cells from the above-described immunodeficient mammal or a progeny thereof.

(8) The present invention relates to immunocompetent cells recovered from the above-described immunodeficient mammal or a progeny thereof.

(9) The present invention relates to a vaccine comprising the immunocompetent cells described in (8) above.

(10) The present invention relates to a method for producing immunocompetent cells, which is characterized in that it comprises recovering the above-described immunocompetent cells from the above-described disease-model mammal or a progeny thereof.

(11) The present invention relates to immunocompetent cells recovered from the above-described disease-model mammal or a progeny thereof.

(12) The present invention relates to a vaccine comprising the immunocompetent cells described in (11) above.

(13) The present invention relates to a human-derived antibody recovered from the above-described disease-model mammal or a progeny thereof.

(14) The present invention relates to a human-derived antibody collected from a culture product obtained by culturing the above-described immunocompetent cells in the presence of an antigen or a stimulator.

(15) The present invention relates to a human-derived antibody recovered from a disease-model mammal or a progeny thereof.

(16) The present invention relates to a vaccine comprising the human-derived antibody described in (15) above.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 4a shows human cells identified as green signals (human X chromosomes). FIG. 4c shows several spleen cells derived from the recipient mice stained with mouse anti-human CD3 (red). FIG. 4b is a view obtained by overlaying panel a on panel c. The blue-stained portion represents a nucleus. FIGS. 4d and 4e show the results obtained by immunohistological staining of spleen tissues collected from mice. FIG. 4f shows a portion of the spleen stained with anti-human CD3 (red). FIG. 4g represents the presence of human APCs.

FIG. 9A shows the presence of HLA$^-$DR$^+$CD11c$^+$ cells in the spleen by flow cytometry. FIG. 9B is a view showing that it was found as a result of immunostaining with an anti-human CD11c antibody that human dendritic cells have estimated morphologic characteristics. The presence of human dendritic cells indicates that structures are formed with human CD19+ cells and CD3+ cells in the spleen of the recipient (FIGS. 9C and 9D).

FIGS. 10A and 10B show nuclei stained with DAPI. These figures also show that human mucosal immunity is present in the intestine sample of the recipient mice, as a result of immunostaining with an anti-human CD3 antibody (A, green) and with an anti-human IgA antibody (B, red). FIG. 10C is a view showing the contours of villus obtained by DIC imaging. FIG. 10D is a view obtained by overlaying A, B, and C. FIG. 10E shows a modal structure observed below the chorion of ileum of an engrafted mouse. FIG. 10F shows the Peyer's patch-like structure stained with an anti-human IgA antibody (red) and an anti-human CD3 antibody (green).

FIGS. 11A and 11B are views showing the BM cells of the recipient mice analyzed by flow cytometry in terms of the presence of human IgG+ cells, before and after the immunization with ovalbumin. FIG. 11C shows a result of the ELISA and indicates the optical density of human IgM (white column in FIG. 11C) and that of human IgG (black column in FIG. 11C) in the serum of the immunized recipients (recipient) or non-immunized recipients (control).

FIGS. 12A to 12C show the cytotoxicity (% Cytotoxicity) of each of the three CD4+ T cell strains in stimulating cells-concentration depending manner (Effector/Target ratio). FIGS. 12D to 12F show the cytotoxicity of each of the three CD8+ T cell strains in stimulating cells-concentration depending manner. The human CD4+ T cell strain was cytotoxic to allogenic LCL (TAK-LCL) used as target cells (FIG. 12, none, (♦). FIG. 12 shows the results of an inhibition assay regarding cytotoxicity caused by human T cells with an anti-HLA class I antibody (anti-HLA class I, (■)) or an anti-HLA-DR antibody (anti-HLA-DR, (▲)). KIN-LCL: a negative control (KIN-LCL, (x)).

BEST MODE FOR CARRYING OUT THE INVENTION

Figure 1:
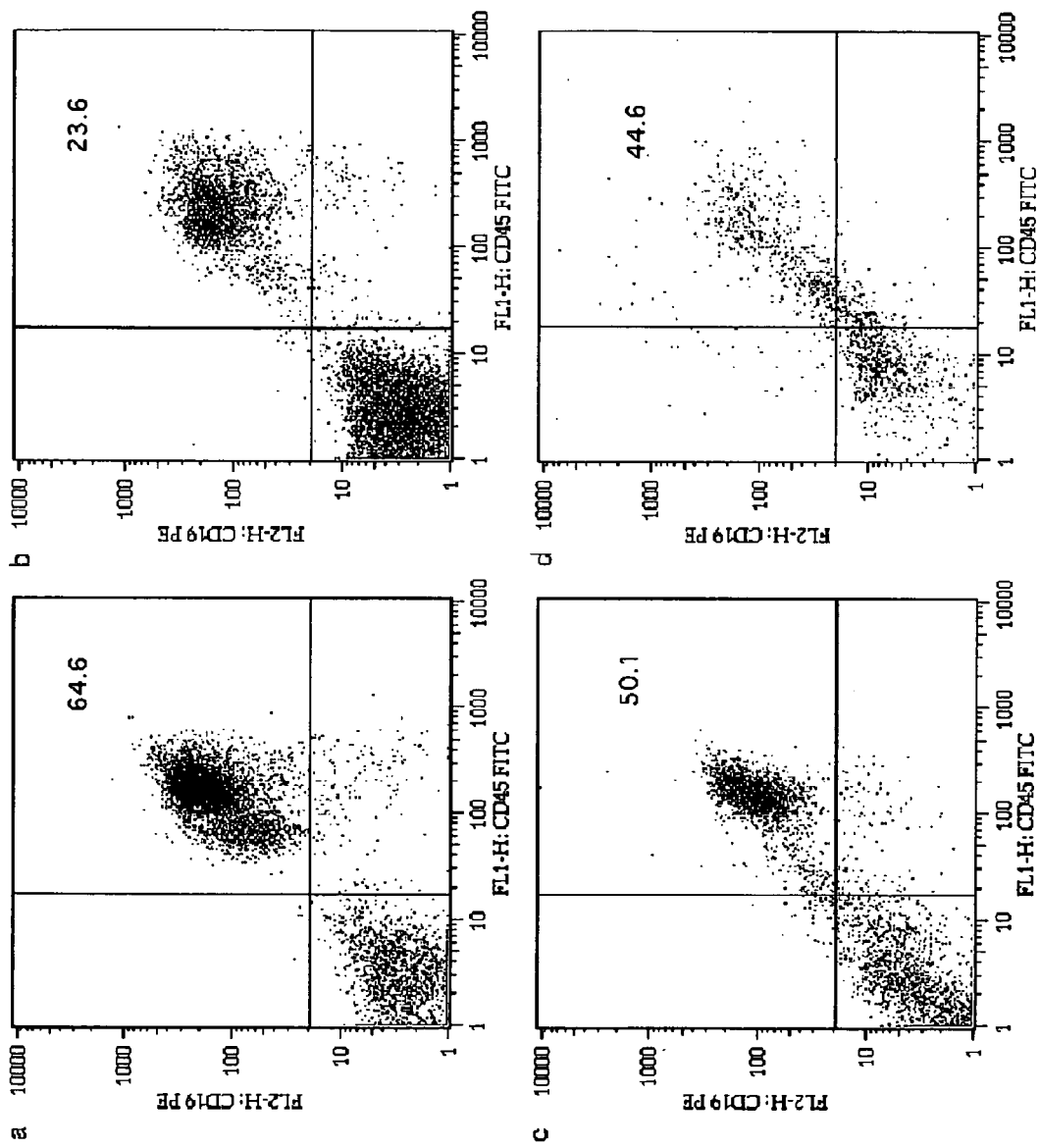
FIG. 1A shows the reconstruction of a human B cell line (CD19$^+$ cells) in recipient mice. a, b, c, and d represent the flow cytometry of cells collected from the bone marrow (BM); the spleen; the peripheral blood (PB); and the lymph nodes (LN), respectively.
FIG. 1B shows the expression of various types of human immunoglobulins in recipient mice. Panels in the first row (e), panels in the second row (f), panels in the third row (g), and panels in the fourth row (h) represent the results obtained by staining the hematopoietic cells derived from the BM, the spleen, the PB, and the LN with FITC-binding IgM (at the first column), IgD (at the second column), IgG (at the third column) and IgA (at the fourth column), and PE-binding CD19 antibody, respectively. The numerical value in each panel represents the ratio (%) of cells expressing each class of immunoglobulin in the CD19$^+$ cells.
Figure 1:
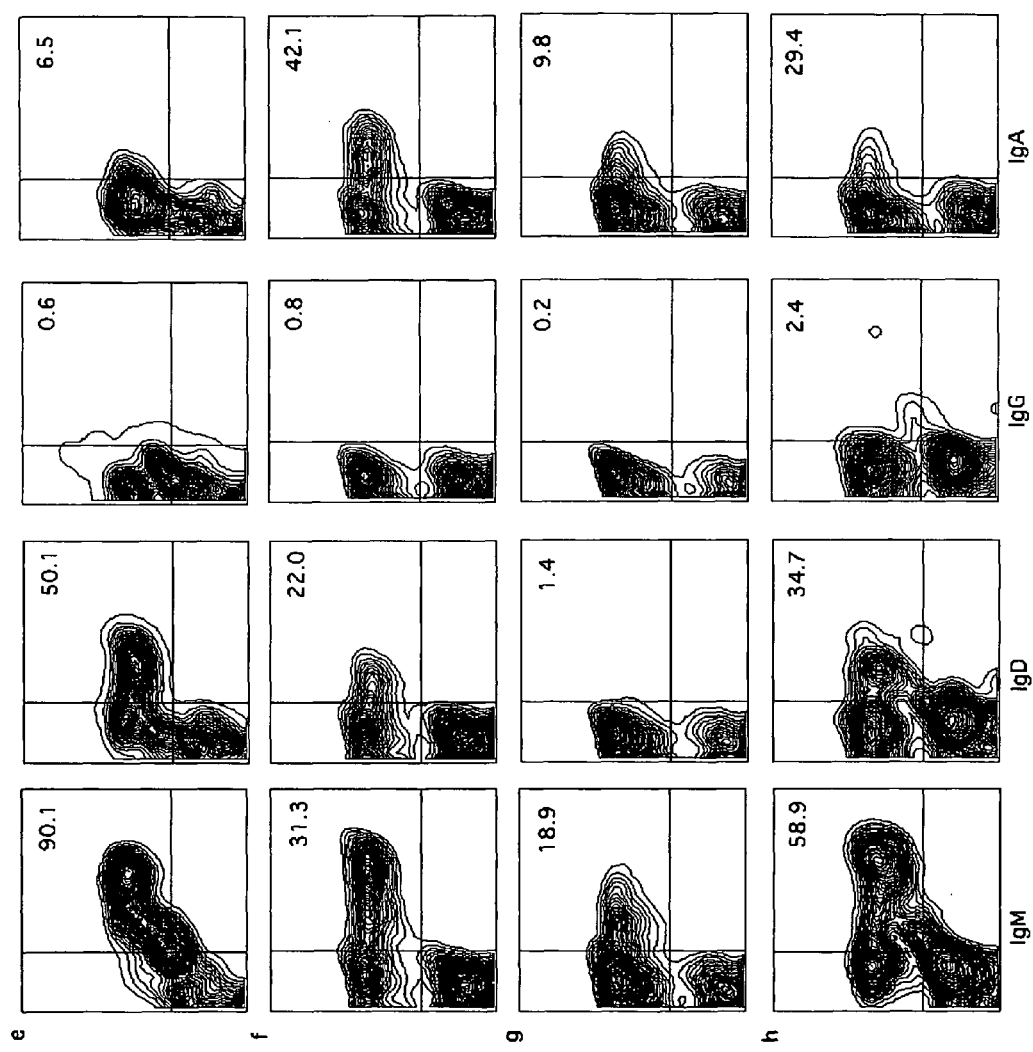

The present invention will be described in detail below.

The present invention has been completed for the purpose of allowing human hematopoietic lineage cells to differentiate and proliferate in the living body of a xenogeneic mammal, so as to reconstruct a human immune system therein. Specifically, the present invention is characterized in that human-derived hematopoietic precursor cells are transplanted into an immature immunodeficient mammal used as a host (for example, an SCID mouse), and in that the human-derived cells are allowed to differentiate and proliferate in the above host. That is to say, a system for constructing a human immune system and hematopoietic system in the body of an immunodeficient mammal can be applied to the generation of a human antibody and the development of a tumoral or viral antigen-specific vaccine.

1. Immature Immunodeficient Mammal

In the present invention, animals used as recipients, into which human-derived hematopoietic precursor cells are transplanted, are immunodeficient mammals other than humans. The term "immature mammal" is used in the present invention to mean mammals including the stages ranging from a fetus and a newborn, up to an individual with a reproductive age. It is preferably a fetus and a newborn baby with an age of 7 days or less, and more preferably a newborn baby with an age of 2 days or less. When an immature immunodeficient mammal is used as a recipient, human immunocompetent cells efficiently proliferate as such an individual grows up. Thus, it is preferable to use such an immature individual in the present invention.

Examples of a mammal may include a mouse, a rat, a hamster, a guinea pig, a sheep, a miniature pig, a pig, and a monkey. Immunodeficient mice are preferable in that there have been many types of model animals and in that the strains thereof have already been established. The term "immunodeficient mouse" is used to mean a severe combined immunodeficiency disease mouse (SCID mouse) that lacks ability to produce T cells and B cells. In particular, an NOD/SCID/β2 microglobulin knockout mouse (NOD/SCID/B2M) and an NOD/SCID/common γ-chain knockout mouse, which do not have the activity of NK cells, are preferable. When such an immature SCID mouse individual is used, human-derived immunocytes and hematopoietic cells can be produced in the living mouse body at high efficiency. The aforementioned SCID mice are commercially available (Jackson Laboratory), and thus persons skilled in the art can easily obtain such mice.

2. Preparation and Transplantation of Cells

Hematopoietic precursor cells to be transplanted can be obtained from cord blood, bone marrow, peripheral blood, G-CSF-mobilized peripheral blood, and ES cell derived mesodermal lineage cells, for example. Of these, cord blood is preferable.

Such cord blood (CB) cells can be obtained in the form of a clinical analyte (for example, an analyte that is to be wasted due to problems regarding the number of cells or family history as a result of clinical tests) from the Metro Tokyo Red Cross Cord Blood Bank (formerly The Japanese Red Cross Central Blood Centre Cord Blood Bank). In addition, born marrow cells can be obtained from the bone marrow bank. Otherwise, such born marrow cells can also be collected by bone marrow aspiration or obtained as cells to be wasted from among the thus collected cells. As peripheral blood, blood collected for using in a general blood test, or blood to be wasted from among such collected blood, can be used. In order to efficiently collect a stem cell population from such peripheral blood, it is also possible to collect it, after stem cells in bone marrow have been mobilized with G-CSF.

Subsequently, monocytes (MNCs) are isolated from the above cells by density gradient centrifugation.

Examples of cells used for transplantation in the present invention may include cells exhibiting CD34 positive (CD34+ cells, CD133+ cells, SP cells, CD34+CD38− cells, and c-kit+ cells). That is, such cells are hematopoietic precursor cells or mature hematopoietic cells. CD34+ cells can be obtained by incubating a sample with an anti-human CD34 microbeads.

The aforementioned sample acting as a source of hematopoietic precursor cells contains cells that have differentiated into T cells, as well as hematopoietic precursor cells. Thus, in order to eliminate such T cells, it is also possible to allow the sample to react with an antibody reacting with a T cell marker. For example, MNCs is incubated with mouse anti-human CD3, CD4 and/or CD8 antibodies. After washing the resultant, the cells are incubated with sheep anti-mouse immunomagnetic beads, so as to recover unbound cells. Since CD3, CD4, and CD8 are all T cell markers (surface antigens), the aforementioned treatment is carried out using antibodies reacting with such antigens, so as to eliminate T cells. The cell surface antigens of the thus obtained precursor cells are CD3 negative (CD3−), CD4 negative (CD4−), and CD8 negative (CD8−). Thereafter, the sample, from which T cells have been eliminated, is incubated with anti-human CD34 microbeads. By this operation, hematopoietic precursor cells presenting CD34$^+$ can be obtained. Thereafter, the cells are subjected to a magnetic column such that the purity of the concentrated CD34$^+$ cells becomes 90% or more.

Mature hematopoietic cells can be obtained utilizing the proliferating ability of hematopoietic stem cells or hematopoietic precursor cells, particularly without the support of a cytokine or the like. However, it is also possible to efficiently obtain a specific fraction by administration of cytokines such as G-CSF, Steel factor, GM-CSF, TPO, or EPO.

The mammal of the present invention can be obtained by previously applying radiation to the entire body of a recipient animal, and then transplanting hematopoietic precursor cells or mature hematopoietic cells, which have been adjusted to a certain amount, into the recipient animal (an NOD/SCID/B2M mouse, NOD/SCID/IL2rg-null mouse, or the like). The number of cells to be transplanted can be determined, as appropriate, depending on the type of an animal. For example, when hematopoietic cells are transplanted into an SCID mouse used as a recipient, the number of the cells to be transplanted is at least $1\times10^3$ per mouse. The upper limit is not particularly limited. Preferably, $1\times10^3$ to $1\times10^7$ cells can be used. It is anticipated that the use of a large number of cells enable differentiation of human cells at higher efficiency.

Such cells are preferably transplanted intravenously. Intraperitoneal, intracardiac or intrahepatic transplantation may be employed. When cells are transplanted intravenously, such cells are injected via facial vein or caudal vein. In such a case, an injection needle with 26 to 30 gages (G) may be used (for example 29 G). For example, it is preferable that $1\times10^5$ of CB cells (CD3$^-$CD4$^-$CD8$^-$CD34$^+$), from which T cells have been eliminated, be transplanted by intravenous injection into an immature NOD/SCID/B2M mouse or NOD.Cg-Prkdc$^{scid}$ mouse, the entire body of which has previously been irradiated with 100 cGY.

After transplantation of the cells, the mouse is bred while carefully maintaining an aseptic environment. The term "maintenance of an aseptic environment" is used to mean that the environment is controlled such that it does not contain pathogenic microorganisms causing infectious diseases or antigenic substances. Thus, this means that mice are bred in an aseptic room at so-called SPF (specific pathogen free) level, are fed an irradiated diet (or a low molecular weight diet), or are fed sterilized water. In the case of mice, if mice are bred in the aforementioned aseptic environment for 2 to 16 weeks, and preferably for 3 to 4 weeks, they can be used for the recovery of immunocytes or immunization. The present invention also provides the thus bred mammals. The mammal of the present invention also includes the progeny thereof. Such progenies can be obtained by common mating, as long as the aforementioned aseptic environment is maintained.

A donor- (human-) derived immune system has been established in the body of the thus obtained "humanized mammal." Thus, human-derived immunocompetent cells or the like can be recovered therefrom. In the present invention, the term "immunocompetent cells" (which is also referred to as immunocytes) is used to mean cells used for establishing immune response. Examples of such cells may include antibody-generating cells and hematopoietic cells. Specific examples may include B cells, T cells, dendritic cells, NK cells, and NKT cells.

Such immunocompetent cells play not only a role for systemic immunity and mucosal immunity (described later), but also a role for protecting a host and tissues thereof in various tissues. For example, in the case of skin, Langerhans cells present an antigen, and T cells and B cells, which are mobilized in the dermis, function. In the case of liver, Kuppfer cells have phagocytic activity. In the case of a nervous system, Microglia cells englobe unnecessary substances, so as to prevent neurodegeneration. Accordingly, in the present invention, immunocompetent cells existing in various tissues also construct a human immune system.

The ratio of such human-derived cells to recipient-derived cells is between 5% and 90%, and preferably between 20% and 90% in the case of hematopoietic cells. Such ratio is between 2% and 80%, and preferably 10% and 80% in the case of antibody-generating cells.

The aforementioned immunocompetent cells are cells derived from a human used as a donor. Various types of physiologically active substances are generated from such cells. Monocytes or dendritic cells function as main antigen-presenting cells. Examples of a physiologically active substance may include a cytokine and an immunoglobulin. Such a cytokine is a protein-type physiologically active substance that controls the proliferation and differentiation of various types of blood cells. Examples of such a cytokine may include interleukin (IL), a colony-stimulating factor (CSF), and chemokine. In recent years, it has been suggested that abnormal secretion of such cytokines or a failure in the control thereof are closely associated with various types of pathologic conditions. In addition, reduction in the generation of such cytokines is highly likely to result in an immunodeficient state in a severe infectious disease. Moreover, such an immunoglobulin (Ig) is a protein having functions and a structure as an antibody. Such an immunoglobulin has such isotypes as IgG, IgM, IgA, IgD, and IgE. The immunoglobulin of the present invention includes all these isotypes. IgG and IgA have their subclasses (G1 to G4, and A1 and A2, respectively). These subclasses are also included in the aforementioned immunoglobulin of the present invention.

B cells are lymphocytes, which express an Ig receptor on the surface or inside thereof. B cells generate immunoglobulins such as IgG, IgM, IgA, or IgD, or cytokines such as IL-6. T cells are lymphocytes, which are associated with immune response and differentiate and mature in thymus gland. Such T cells generate IL-2 to IL-6, IL-9, IL-10, IL-13, IL-14, IL-16, or the like. Dendritic cells are cells having dendrites, which act as auxiliary cells (accessory cells) when immune response initiates. Such dendritic cells express a class II major histocompatibility (MHC) antigen, and thus function as antigen-presenting cells to helper T cells. NK (natural killer) cells exhibit cytotoxicity to virus-infected cells or tumor cells without restriction by the MHC antigen. NKT (natural killer T) cells are cells having a T cell receptor and an NK cell marker (for example, CD16 or CD56). Such NKT cells generate IFN-γ or IL-4 as a result of stimulation by a galactosylceramide (αGalCer) that is a glycolipid.

3. Confirmation of Chimerism and Generation of Antibody and Vaccine

Expression of human-derived cells in a recipient animal can be confirmed by collecting peripheral blood, bone marrow cells, or other immune tissues from the recipient animal, and then confirming that the thus collected items are derived from the human.

For example, when an immunodeficient mouse is used as a recipient, peripheral blood is collected from the retroorbital plexus thereof, or bone marrow cells are collected from femur and tibia thereof, 3 weeks to 3 months after the transplantation. In addition, spleen, lymph node, and thymus gland thereof are excised and then fragmented. Thereafter, the separated cells are passed through a mesh filter, so as to obtain a single cell suspension. These cells are then subjected to the expression analysis of human CD45 (a leukocyte common antigen, that is, a main membrane glycoprotein of hematopoietic cells), using FACSCalibur or FACSVantage (Becton Dickinson). As a result, it is identified that the cells are hematopoietic cells derived from the donor. It is also possible to stain the cells with a mouse anti-human antibody or the like.

Moreover, in the mammal of the present invention, an immune system derived from a human as a donor has been established. In particular, in the case of mice, the bone marrow, spleen, lymph node, peripheral blood, and thymus gland thereof have been substituted with human cells by almost 100%. (Hereinafter, such mice are referred to as "humanized mice" in the present invention, at times). Accordingly, B cells (antibody-generating cells) that are immunocompetent cells, spleen cells containing such B cells at a high rate, or other cells are stimulated with an antigen or a suitable stimulator, so as to generate a human-derived antibody. For example, the immunocompetent cells of the present invention are cultured in the presence of bacteria, viruses, or tumors (including tumor cells, antigenic peptides, or the like), so as to promote the generation of a human-derived antibody. Since the surface antigen of B cells exhibits CD19 positive (CD19$^+$), the ability to generate an antibody is measured by analyzing with a cell sorter the expression of IgM, IgG, IgD, and IgA in the CD19$^+$ cells.

Furthermore, the mammal of the present invention is immunized with a certain antigen or a suitable stimulator, and an antibody is then collected from the obtained immunocytes, so as to obtain a donor- (human-) derived antigen-specific antibody. For example, bacteria, viruses, or tumors (including tumor cells, antigenic peptides, or the like) are administered to the mammal of the present invention or a progeny thereof. Otherwise, tissues or cells obtained from the mammal of the present invention or a progeny thereof are cultured in the presence of bacteria, viruses, or tumors (including tumor cells, antigenic peptides, or the like). Thereby, the generation of a human-derived antibody is promoted, or a vaccine can be developed. It has been known that dendritic cells pulsed (stimulated) by the aforementioned stimulation are able to efficiently induce T cells. Thus, dendritic cells pulsed in a living body are selected, and such cells can also be used as vaccines.

In the case of mice, the amount of such an antigen or a suitable stimulator administered per animal is between 10 μg and 1 mg. Such amount is adjusted, as appropriate, depending on the presence or absence of an adjuvant. Examples of such an adjuvant may include Freund's complete adjuvant (FCA), Freund's incomplete adjuvant (FIA), and aluminum hydroxide.

The type of an antigen or a suitable stimulator is not particularly limited. Examples may include a protein, a peptide, and a lectin.

The site of administration is vein, subcutis, footpad (food pad), or abdominal cavity. Immunization interval is not particularly limited. Immunization is carried out 1 to 3 times at intervals of several days to several weeks, and preferably at intervals of 1 to 2 weeks. Thereafter, approximately 1 to 2 weeks after the final immunization, an antibody titer in serum or blood plasma is measured, and antiserum or antiplasma is obtained. Such an antibody titer can be measured by enzyme-linked immunosorbent assay (ELISA), radioimmuno assay (RIA), or the like.

When purification of an antibody from such antiserum or antiplasma is necessary, known methods such as the ammonium sulfate salting-out method, ion exchange chromatography, gel filtration, or affinity chromatography, are appropriately selected, or these methods are used in combination, so as to purify an antibody.

When a large animal, and in particular, an immunodeficient pig is used as a recipient, it brings on an advantage in terms of generation of a large amount of antibody. Examples of such a large animal may include immunodeficient animals produced by the gene knockout of IL7R, IL2R common gamma chain, Jak/Stat, RAG-1, RAG-2, etc.

On the other hand, in order to develop a high-quality vaccine, it is desired that a small animal be used as a recipient. Using such a small animal, the degree of the effective antitumoral effect of various peptides or antigens in the living body of the animal of the present invention having a human immune system, or whether or not such peptides or antigens have peptide recognition efficiency, can easily be determined. In addition, using a system for evaluating the in vivo activity of leukemic cells that has been developed by the present inventors, it is also possible to evaluate the degree of effectiveness of the developed vaccine, dendritic cells, or T cells, on tumor cells proliferated in vivo, such as leukemic cells.

Accordingly, the present invention provides a method for screening for an immune-related pharmaceutical, which is characterized in that it comprises administering a test substance to the animal of the present invention (including an immature individual, a living body, a progeny, and a model animal), and evaluating the effectiveness of the test substance. Representative examples of such an "immune-related pharmaceutical" may include an antibody pharmaceutical and a vaccine (peptides, dendritic cells, etc.). Antiviral agents and agents used for infectious diseases, such as antibiotics, are also included in such an immune-related pharmaceutical. Further, a wide range of liquid factors involving cytokine therapy is also included therein. The dosage and administration method of such an immune-related pharmaceutical can be determined based on body surface area, body weight, and sex. In particular, main administration routes of such a pharmaceutical are intravenous, intramedullary, intraperitoneal, intrahepatic, and subcutaneous administrations. Such an immune-related pharmaceutical is used for an extremely wide range of diseases. Examples of such diseases may include neoplastic disease, autoimmune disease, viral disease, fungous disease, nervous disease, parasitic disease, intractable disease, bacterial disease, Mycobacterium disease, collagen disease such as articular rheumatism or SLE, hematopoietic organ malignant disease such as leukemia or lymphoma, solid tumor, benign hematopoietic organ and solid tumor disease, pollinosis, allergy, atopy, and AIDS.

Furthermore, the present method is useful in confirming immune response to the human antibody of the present invention and the safety thereof against allergy (in particular, at a preclinical test stage).

In the animal of the present invention or a progeny thereof, the mucosal immunity, alimentary canal immunity, and respiratory tract immunity thereof are also constructed by a human immune system. The term "mucosal immunity" is used herein to mean immunity, which generates secretory immunoglobulins such as secretory IgA and is found in tissues containing a large number of T cells of lymph follicle or Peyer's patch specific to mucosa. The term "alimentary canal immunity" is used herein to mean an entire system for eliminating antigens that are unnecessary or harmful for a body from among antigens such as bacteria incorporated into the body by ingestion. The term "respiratory tract immunity" is used herein to mean immunity, which generates secretory immunoglobulins, as with the alimentary canal immunity, and includes the total immune response to extrinsic antigens entering through the airway (including nasal cavity, bronchus, and alveoli pulmonis).

The use of the mucosal immune system of the humanized animal of the present invention enables the development of oral vaccines, elucidation of alimentary canal infectious disease, elucidation of the pathologic conditions of food allergy, the development of allergy medicines, etc. The present immune system is applied to an extremely broad range of purposes. For example, as oral vaccines, vaccines for polio have been well known from a long time ago. However, it is desired that vaccines used for infectious diseases causing lethal food poisoning, such as O157, cholera, or dysentery, be developed. A body fluid (mainly, serum) or cells recovered from the disease-model animal of the present invention or a progeny thereof, or the immunocompetent cells of the present invention, can be used as the aforementioned vaccine.

It is said that inflammatory bowel diseases such as Crohn's disease or ulcerative colitis are caused by the abnormality of immune systems. Accordingly, the animal, method, antibody, and vaccine of the present invention can be applied to elucidation of the pathologic conditions of such diseases, or the development of a new therapy involving transplantation of stem cells or injection of T cells, in future.

In addition, the animal of the present invention or a progeny thereof can also be used as a disease-model animal (in particular, as an infectious disease-model animal or tumor-model animal). Among them, the animal of the present invention or a progeny thereof is anticipated to use as a virus disease-model animal. In particular, in the case of viruses, since such viruses are specific to species, mice are not infected with viruses that seem to be important at the current clinical site, such as human HIV or HSV. Accordingly, the previous experiments have been problematic in that infection experiments have been conducted only using the same virus strains such as murine herpes virus or murine retrovirus, and in that HIV has not been directly used. Since the model animal of the present invention has a human immune system, disease-models can be produced by infecting mice with bacteria, fungi, or viruses. The disease-model of the present invention can be produced by administering various amounts of antigens to animals at a unit between μg and mg. As stated above, examples of an administration route may include intravenous, intramedullary, intrahepatic, intraperitoneal, and subcutaneous injection. Examples of an antigen may include bacteria, fungi, viruses, OVA, proteins, peptides, and cells.

For example, the present inventors have observed viruses such as HIV or HTLV-1 in the living body of a mouse, and the inventors have already efficiently confirmed that human CD4 positive cells used as host cells of such viruses differentiate, for example, from stem cells in the mouse body, and that mature T cells directly adhere thereto. Accordingly, the disease-model animal of the present invention is anticipated to use for infection experiments regarding infection with various viruses causing clinical problems including the aforementioned viruses.

4. Tests Regarding Other Chimerisms (1) Histological Analysis

A recipient mouse is dissected. Thereafter, tissues are immobilized or frozen. Tissues immobilized with paraformaldehyde are preferably dehydrated with stepwise concentrations of alcohol and are then embedded in paraffin. Sections are prepared using a microtome, a cryostat, or the like. Each of the sections is then subjected to common immunohistological staining.

(2) Fluorescent In Situ Hybridization (FISH) Method

The FISH method is a known technique of determining gene locus on chromosome. This method comprises allowing single-stranded probe DNA labeled with a fluorescent substance or the like to hybridize with chromosomal DNA at a complementary site thereof, and then identifying a specific site in an object cell or the like under a microscope.

EXAMPLES

The present invention will be more specifically described in the following examples. However, these examples are not intended to limit the present invention.

Example 1

Transplantation of Human Hematopoietic Cells into Immunodeficient Mice

Cord blood (CB) cells were obtained from the Metro Tokyo Red Cross Cord Blood Bank. After obtaining written informed consent, CB cells were collected from cord blood to be wasted. Thereafter, monocytes (MNCs) were isolated from the CB in a density gradient manner (lymphocyte isolation medium, ICN Biomedicals) by centrifugation at 370×g for 30 minutes. The obtained MNCs were then incubated together with mouse anti-human CD3, CD4, and CD8 antibodies (BD Immunocytometry) at 4° C. for 30 minutes. After washing, the cells were incubated together with sheep anti-mouse immunomagnetic beads (DINAL) at 4° C. for 30 minutes, so as to recover unbound cells. In order to isolate a $CD34^+$ population, T cell-eliminated sample was incubated together with anti-human CD34 microbeads (Miltenyi Biotech) for 40 minutes (in accordance with protocols provided by manufacturers). The cells were passed through a magnetic column twice. As a result, the purity of the concentrated $CD34^+$ cells was found to be 90% or more.

The thus prepared CB cells ($CD3^-CD4^-CD8^-CD34^+$; $1\times10^5$ cells) were transplanted by intravenous injection into newborn NOD/SCID/B2M mice (Jackson Laboratory), the entire bodies of which had previously been irradiated with 100 cGy, so as to produce mice, in which a human immune system including human-derived immunocytes was constructed.

Example 2

Analysis of Human-Derived B Lineage Cells in Living Bodies of Mice

In order to examine the presence or absence of reconstruction of human lymph cells in the living bodies of mice, multiple analyses of hematopoietic tissues were conducted in terms of the transplantation level of $CD19^+$ cells (B cells) that are human $CD45^+$ cells.

After transplantation, recipient mice were bred for 3 months, and on the $3^{rd}$ month, it was analyzed regarding whether or not human-derived B lineage cells existed in the bone marrow (BM), spleen, peripheral blood (PB), and lymph nodes (LN) of the recipient mice. The BM, spleen, PB, and LN were stained with FITC-binding immunoglobulin and PE-binding CD19.

The results are shown in FIGS. 1A and 1B. In FIG. 1A, a, b, c, and d represents the flow cytometry of cells collected from the BM; the spleen; the PB; and the LN, respectively. In each of lymphoid tissues, human $CD45^+CD19^+$ cells were identified at a high level. Each of the numerical values shown in a to d of FIG. 1A (64.6, 23.6, 50.1, and 44.6, respectively) represents the ratio (%) of the $CD45^+CD19^+$ cells to the entire cells collected from each tissue.

In addition, in 16 panels shown in FIG. 1B, panels in the first column (e), panels in the second column (f), panels in the third column (g), and panels in the fourth column (h) represent the results obtained by staining the hematopoietic cells derived from the BM, the spleen, the PB, and the LN with FITC-binding IgM (at the first line), IgD (at the second line), IgG (at the third line) and IgA (at the fourth line), and PE-binding CD 19 antibody, respectively. The numerical value in each panel represents the ratio (%) of cells expressing each class of immunoglobulin in the CD19+ cells. For example, the numerical value, 90.1, found in the line of (e) and in the first column represents the ratio of bone marrow-derived cells expressing IgM.

From these results, it was revealed that human-derived immunoglobulins are expressed at a high rate in the tissues of each of BM, spleen, PB, and LN.

Subsequently, in order to examine the antigen-specific response of human lymphoid cells surviving in mice, the mice produced in Example 1 were immunized with 100 μg of ovalbumin (OVA), and the presence of OVA-specific IgM and IgG was then analyzed by ELISA. The blood plasma of recipient mice was diluted 10 times (for IgM analysis) or 3 times (for IgG analysis), and the absorbance of each sample was then measured. At the same time, B cells were collected from the recipient mice, and the cells were then cultured in RPMI/FCS (fetal bovine serum)/Pokeweed mitogen medium for 5 days. Thereafter, the immunoglobulin contained in the culture supernatant was measured by ELISA. As a negative control, the immunoglobulin contained in human serum was measured.

Figure 2:
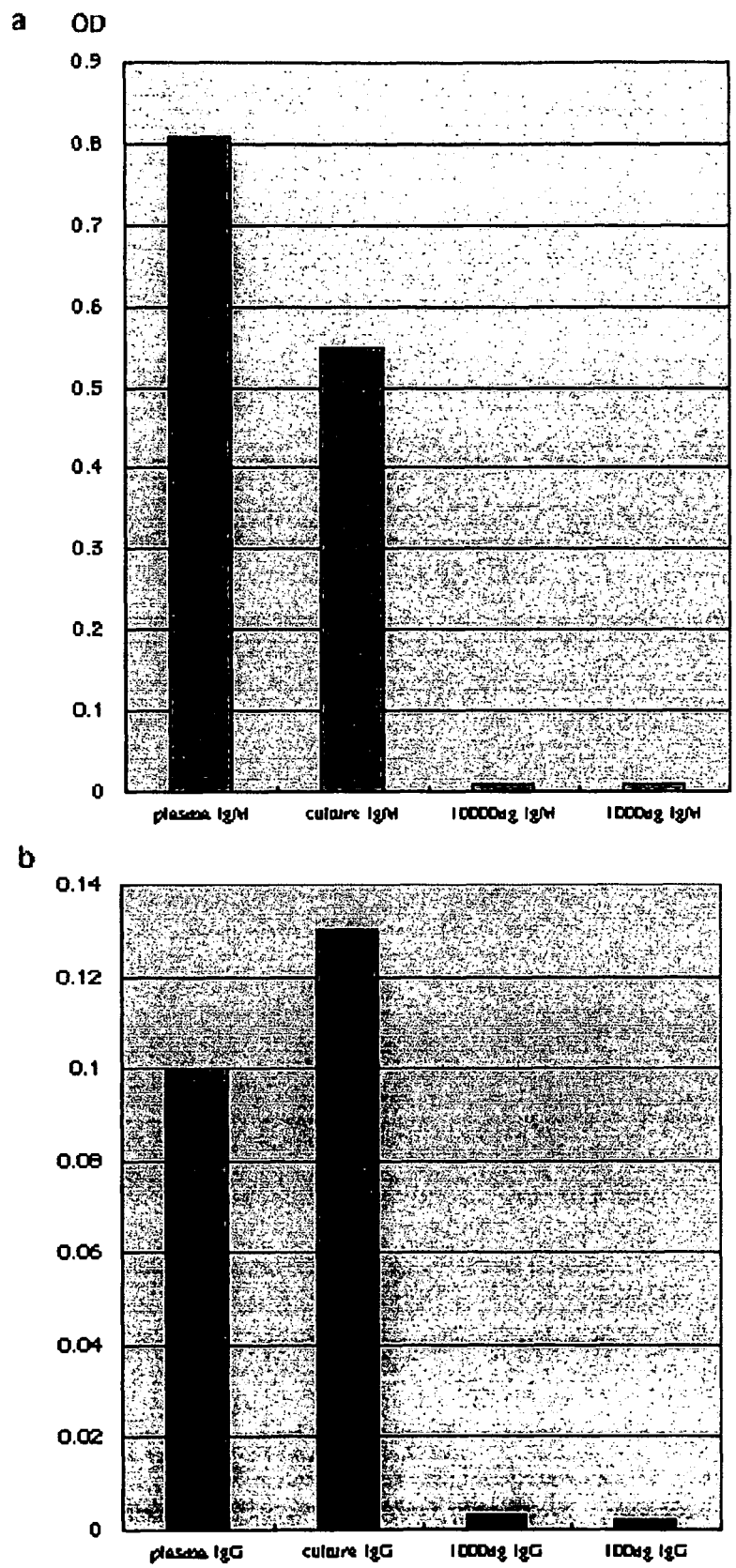
FIG. 2 shows the results of ELISA performed on OVA-specific IgM. Panel a represents the results of IgM, and panel b represents the results of IgG. The bars in the figure represent blood plasma, culture supernatant, negative control 1 (human serum), and negative control 2 (a tenth part of the serum as negative control 1), from the left.

The results are shown in FIG. 2. In FIG. 2, panel a represents the results of IgM, and panel b represents the results of IgG. The bars in the figure represent blood plasma, culture supernatant, negative control 1 (human serum), and negative control 2 (a tenth part of the serum as negative control 1), from the left. FIG. 2 shows that antigen-specific IgM and IgG were generated at a high rate.

Example 3

Differentiation and Maturation of B Lineage Cells

Using a cell sorter, human CD19+ cells (B cells) were collected from the peripheral blood (PB), bone marrow (BM), and spleen of recipient mice, and the expression of IgM, IgG, IgD, and IgA in the B cells was examined. The surface expression of IgM/IgD in the CD19+ cells was 90.0%/54.0% in the case of PB, 19.7%/3.4% in the case of BM, and 59.0%/22.7% in the case of spleen.

Using pokeweed mitogen (PWM), the spleen cells were further cultured in a test tube for 5 days. In addition, recipient mice immunized with 100 μg/ml of OVA were also produced. Subsequently, secretion of human immunoglobulins into the culture supernatant and blood plasma was examined by ELISA (Table 1). After completion of the culture with PWM for 5 days, the medium (supernatant) contained 114 ng/ml to 19.8 μg/ml of IgM, 2.6 to 47.6 ng/ml of IgG, and 1.9 to 5.7 ng/ml of IgA (Table 1).

TABLE 1

Generation of human immunoglobulins

| Sample | Plasma/immunogen | IgM | IgG | IgA |
|---|---|---|---|---|
| 1 | Plasma/OVA | 225000 | 823 | 553 |
| 2 | Medium/OVA | 19800 | 47.6 | 5.7 |

TABLE 1-continued

Generation of human immunoglobulins

| Sample | Plasma/immunogen | IgM | IgG | IgA |
|---|---|---|---|---|
| 3 | Plasma | 23000 | 13 | 40 |
| 4 | Medium | 114 | 2.6 | 1.9 |
| 5 | Plasma | 47700 | 4.1 | 10.3 |
| 6 | Plasma | 17200 | 5 | 9.4 |

(Unit of amount generated: ng/ml)

Blood plasma collected from the recipient mice contained 17.2 to 225 μg/ml of IgM, 4.1 to 823 ng/ml of IgG, and 9.4 to 553 ng/ml of IgA.

As shown in Table 1, when recipient mice were immunized with OVA, human B cells secreted large amounts of IgM, IgG, and IgA, including OVA-specific IgM. Accordingly, in the present example, it was shown that human B cells generated in newborn NOD/SCID/B2M mice maturate and then generate human-derived IgM and IgD, and that the above cells have functions to generate antigen-specific human-derived IgM, IgG, and IgA.

Based on these findings, it was revealed that B cells obtained from the mouse of the present invention are not only used as human antibody-generating cells, but also useful for generating human immunoglobulins (monoclonal antibodies) acting on pathogenic microorganisms causing severe infectious diseases or on tumors.

Example 4

Analysis of Human-Derived T Lineage Cells in Living Bodies of Mice

In the present example, flow cytometric analysis was carried out regarding the presence of human T cells (CD45 and CD3) in the BM, spleen, and PB of recipient mice.

Figure 3:
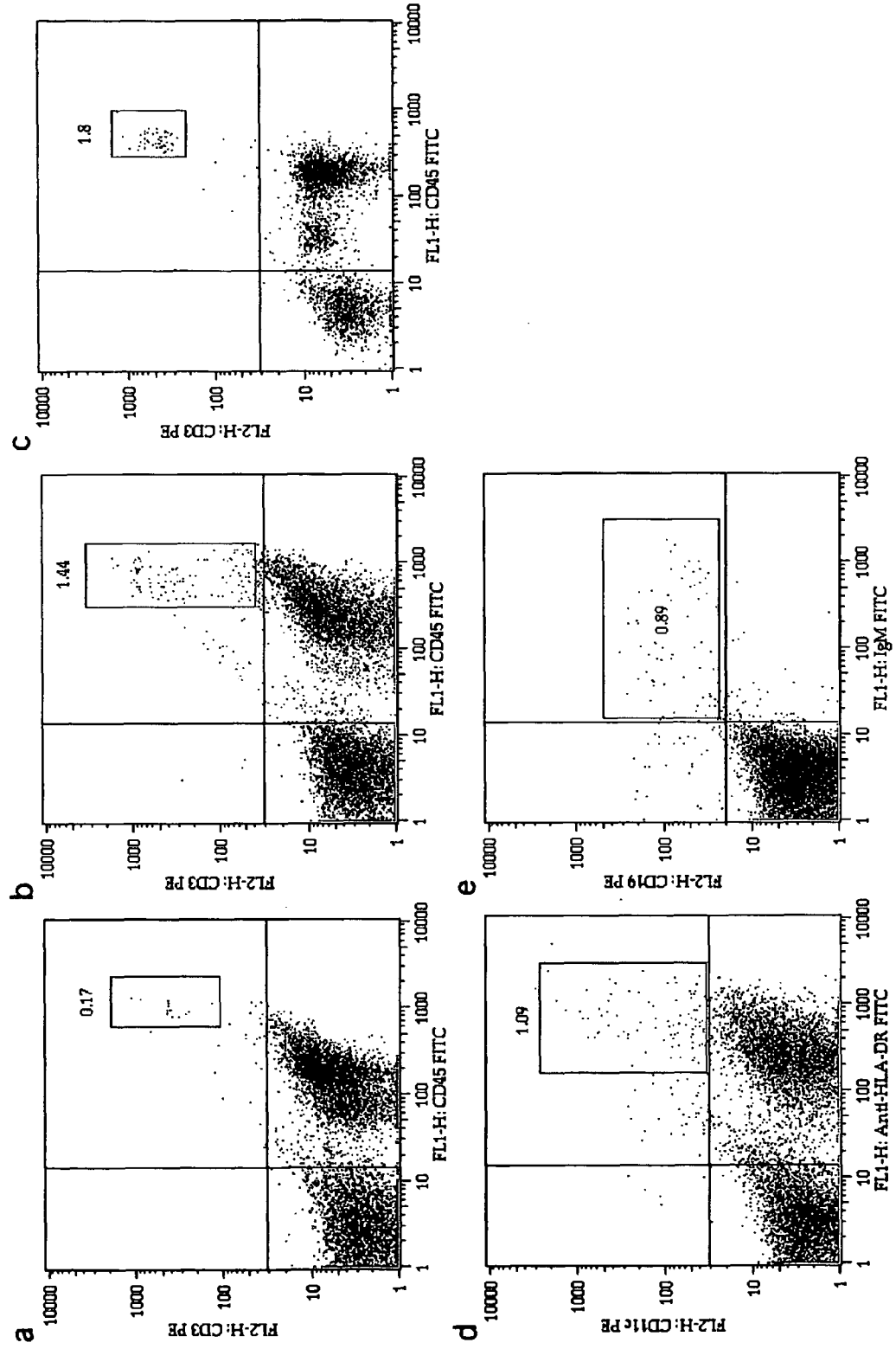
FIG. 3 shows the reconstruction of a human T cell line in the bone marrow, spleen, and peripheral blood of recipient mice. The panels in FIGS. 3a to 3c represent the analysis results of BM (a), those of spleen (b), and those of PB (c), respectively. The panels in FIGS. 3d and 3e represent the analysis results of BM (d) and those of thymus gland (e), respectively.

The results are shown in FIG. 3. The panels in FIGS. 3a to 3c represent the analysis results of BM (a), those of spleen (b), and those of PB (c), respectively. When compared with B cells, the number of T cells was smaller, but the t cells differentiated. Three months after the transplantation into the recipient mice, the ratio of CD3+ cells was found to be 0.17% in the case of BM, 1.44% in the case of spleen, and 1.8% in the case of PB.

The ratio of antigen-presenting cells (APCs) with phenotype HLA−DR+CD11c+ was found to be 1.09% in the case of BM (FIG. 3d). Moreover, in thymus gland, CD19+IgM+ B cells were identified (FIG. 3e).

Example 5

FISH Analysis and Immunofluorescence Analysis of Lymphoid Tissues

In order to examine distribution of human lymph cells in situ, using spleen derived from the recipient mice, double FISH analysis was carried out in terms of human and mouse chromosomes. FISH was carried out in accordance with a common method (Vysis). A laser scanning confocal microscope (LSM510Meta: Carl Zeiss) was used for sample analysis.

Figure 4:
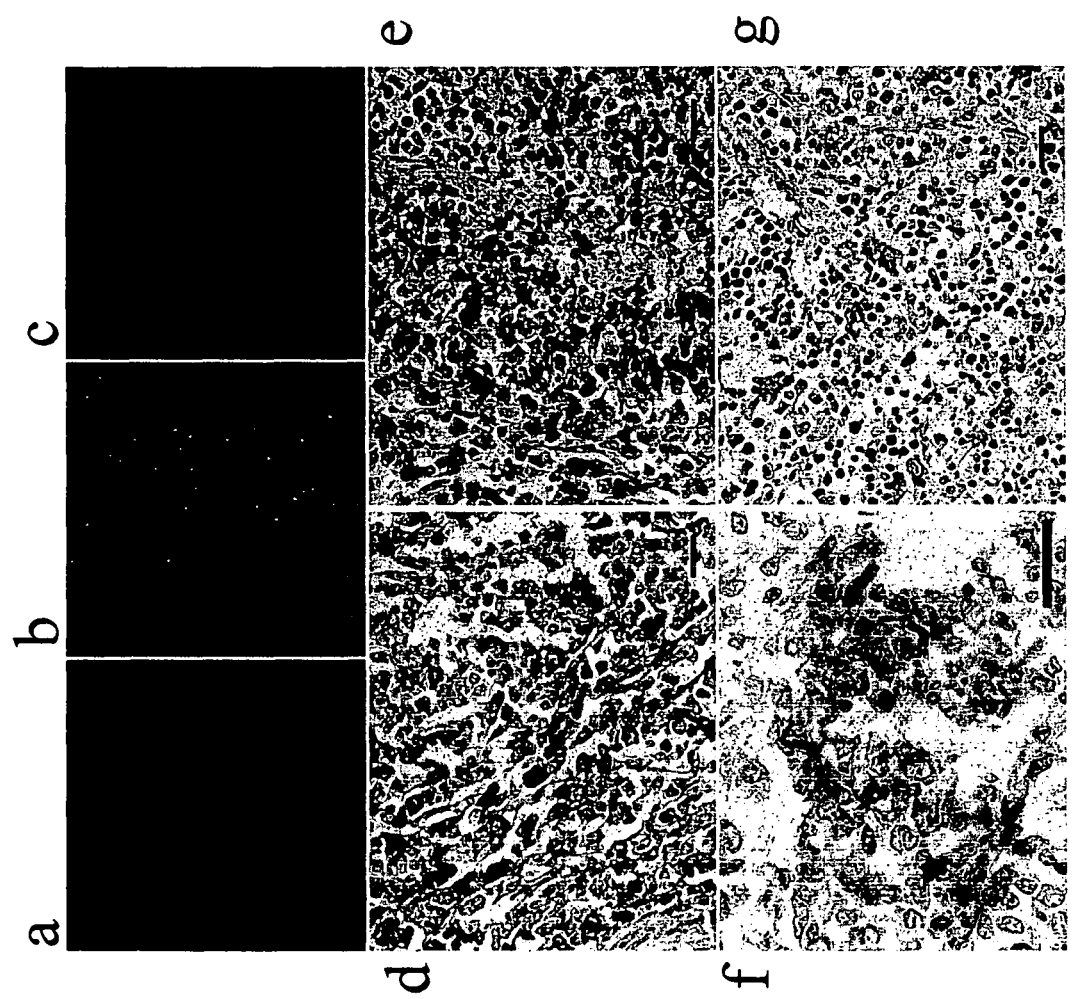
FIG. 4 shows the results obtained by the FISH analysis and immunohistological analysis of lymphoid tissues.

From an experiment using human X chromosome probe, human cells were obtained at a high frequency, which did not contradict the results of FACS analysis. From the results of double FISH analysis using human and mouse X chromosomes, it became clear that interstitial cells derived from mice also exist in the spleen (FIG. 4).

Human cells were identified as green signals (human X chromosomes) (FIG. 4a). Several spleen cells derived from the recipient mice were stained with mouse anti-human CD3, and such cells became red (FIG. 4c). FIG. 4b is a view obtained by overlaying panel a on panel c. The blue-stained portion represents a nucleus.

Before transplantation, recipient mice lacked all mature lymph cells. By transplanting human CB-derived T cell-eliminated CD34+ cells into the mice, human-derived lymphoid tissues were successfully reconstructed in the mice.

In addition, tissue samples were subjected to immunohistological staining. The results obtained by immunohistological staining of spleen tissues collected from mice are shown in FIGS. 4d and 4e. A majority of spleen cells were stained with anti-human IgM positive (d) and anti-human IgD positive (e), and they became red. Thus, it was revealed that human-derived spleen cells survived therein at an extremely high rate. Moreover, the spleen tissues were stained with mouse anti-human CD3. As a result, a portion of the spleen was stained with anti-human CD3, and it became positive (red) (FIG. 4f). Thereafter, a specific antibody to follicular dendritic cells was used to conduct immunostaining, and the presence of human APCs was also confirmed (FIG. 4g).

Example 6

Reconstruction of Multicellular-Lineage of Human Cells in Xenogeneic Host

The present example was given to develop "humanized mice" that are reconstructed with hematopoietic cells. Newborn NOD/SCID/IL2rg-null (NOD.Cg-Prkdc$^{scid}$IL2rg$^{tm1Wjl}$/Sz) mice (Jackson Laboratory) were used as recipient mice, into which human CB hematopoietic stem cells/precursor cells were to be transplanted. Transplantation of human hematopoietic stem cells into the above mice was carried out by almost the same method as that described in Example 1. Cord blood (CB) cells were obtained from the Metro Tokyo Red Cross Cord Blood Bank. After obtaining written informed consent, CB cells were collected from cord blood to be wasted. Using mouse anti-human CD3, CD4, CD8, CD11b, CD19, CD20 and CD56, and a glycophorin A monoclonal antibody (BD Immunocytometry), Lin (lineage-antigen) positive cells were eliminated from monocytes (MNCs). In order to isolate a CD34+ hematopoietic stem cell population at high purity, the monocytes were incubated together with anti-human CD34 microbeads (Miltenyi Biotech) at 10° C. for 30 minutes (in accordance with protocols provided by manufacturers). The cells were passed through a magnetic column twice. As a result, the purity of the concentrated CD34+ cells was found to be 95% or more. Thus, the ratio of CD19+ cells and CD3+ cells therein became 0.1% or less.

Before transplanting the thus prepared Lin−CD34+ cells ($1 \times 10^5$ cells) by intravenous injection into newborn NOD/SCID/IL2rg-null mice and NOD/SCID/β2m$^{null}$ mice, the entire bodies of the mice were irradiated with 100 cGy.

NOD/SCID/IL2rg-null mice completely lack mature B cells and T cells, and the activity level of NK cells is extremely low in such mice. Accordingly, using such mice as recipients, the risk of rejecting xenogeneic cells can be reduced. In addition, since newborn mice are immunologically immature, human stem cells are fixed while the newborn recipients grow up, and thereafter, differentiated hematopoietic cells can be obtained therefrom. Actually, $1 \times 10^5$ of Lin−CD34+ cells were efficiently transplanted into the BM of the recipient mice, and multicellular-lineage differentiated cells were generated in the primary or secondary lymphoid organ.

Three months after the transplantation, human-derived B lineage cells in the living bodies of the recipient mice were analyzed in the same manner as in Example 2. Using FACS-Calibur (Becton Dicinson), the expression of human CD45 and the lineage marker thereof was analyzed. As a result, a recipient mouse hematopoietic system comprises all components for a human hematopoietic system. In the BM of the recipient mice, human GPA+ erythrocytes were present at a frequency of 9.5±6.2% (n=5), and human CD41+ megakaryocytes were present at a frequency of 1.64±0.42% (n=5) (FIG. 5A).

Figure 5:
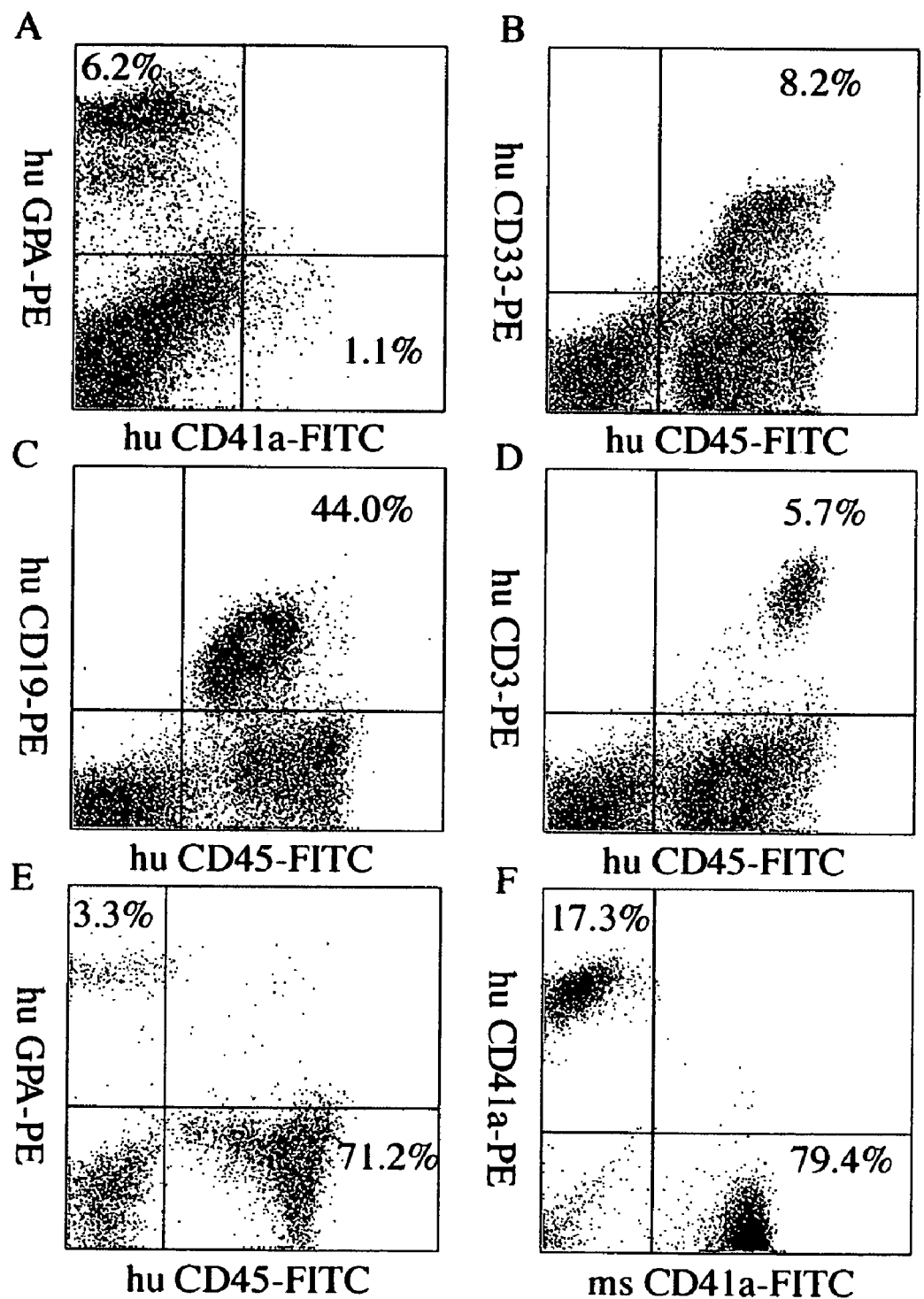
FIG. 5 shows the identification of human erythrocyte compositions in the bone marrow (BM) of NOD/SCID/IL2rg-null mice. A: human GPA$^+$ erythrocytes and human CD41$^+$ megakaryocytes; B: CD33$^+$ spinal cord cells; C: CD19$^+$B cells; D: CD3$^+$T cells; E: human mature erythrocytes; F: human mature thrombocytes.

In addition, human CB-derived Lin−CD34+ cells generated CD33+ spinal cord cells, CD19+ B cells, and CD3+ T cells, in the BM (FIGS. 5B to 5D, respectively).

In order to evaluate the dominance of the NOD/SCID/IL2rg-null mice, in terms of transplantation level, the above mice were compared with NOD/SCID/β2m$^{null}$ mice (NOD/LtSz-Prkdc$^{scid}$/Prkdc$^{scid}$/B2m$^{null}$) (Jackson Laboratory), which are considered to have the best transplantation efficiency among the existing mouse lines. $1 \times 10^5$ of Lin−CD34+-derived human CB cells were transplanted into the NOD/SCID/β2m$^{null}$ mice and NOD/SCID/IL2R-γc$^{null}$ mice. Three months after the transplantation, the transplantation level of human CD45+ cell were analyzed in the BM, spleen, and peripheral blood (PB) of the recipient mice.

As a result, the transplantation level of the human cells in the PB of the NOD/SCID/IL2rg-null mice (68.9±11.6%, n=5) was significantly higher than that in the PB of the NOD/SCID/β2m$^{null}$ mice (12.4±5.9%, n=5). The presence of human mature erythrocytes (FIG. 5E) and human mature thrombocytes (FIG. 5F) was confirmed therein together with human leukocytes. The NOD/SCID/IL2rg-null mice also exhibited high transplantation levels in terms of in the BM thereof (72.9±9.8%, n=5) and in the spleen thereof (54.5±8.0%, n=5) (Table 2).

Since human cells circulate in the peripheral blood, as well as in the BM and spleen, in particular, by stimulating the cells with an extrinsic antigen or a cytokine, the migration or flow of the human cells can be analyzed.

TABLE 2

Chimerization of human CD45+ cells in NOD/SCID/β2m$^{null}$ mice and NOD/SCID/IL2rg-null mice

| Strain | Mouse | BM | Spleen | PB |
|---|---|---|---|---|
| NOD/SCID/β2m$^{null}$ | 1 | 46.1% | 22.0% | 10.4% |
| | 2 | 31.5% | 24.3% | 11.6% |
| | 3 | 18.1% | 20.7% | 6.9% |
| | 4 | 30.4% | 31.2% | 20.7% |
| | mean +/− SD | 31.5 +/− 11.5% | 22.6 +/− 4.7% | 12.4 +/− 5.9% |

TABLE 2-continued

Chimerization of human CD45+ cells in NOD/SCID/β2m$^{null}$ mice and NOD/SCID/IL2rg-null mice

| Strain | Mouse | BM | Spleen | PB |
|---|---|---|---|---|
| NOD/SCID/IL2rg-null | 1 | 70.9% | 66.8% | 71.2% |
| | 2 | 81.4% | 47.1% | 81.7% |
| | 3 | 58.8% | 49.5% | 50.1% |
| | 4 | 83.1% | 51.1% | 68.0% |
| | 5 | 70.1% | 58.1% | 73.3% |
| | mean +/− SD | 72.9 +/− 9.8% | 54.5 +/− 8.0% | 68.9 +/− 11.6% |

Example 7

Differentiation of Human Immune System in NOD/SCID/IL2rg-null

Figure 6:
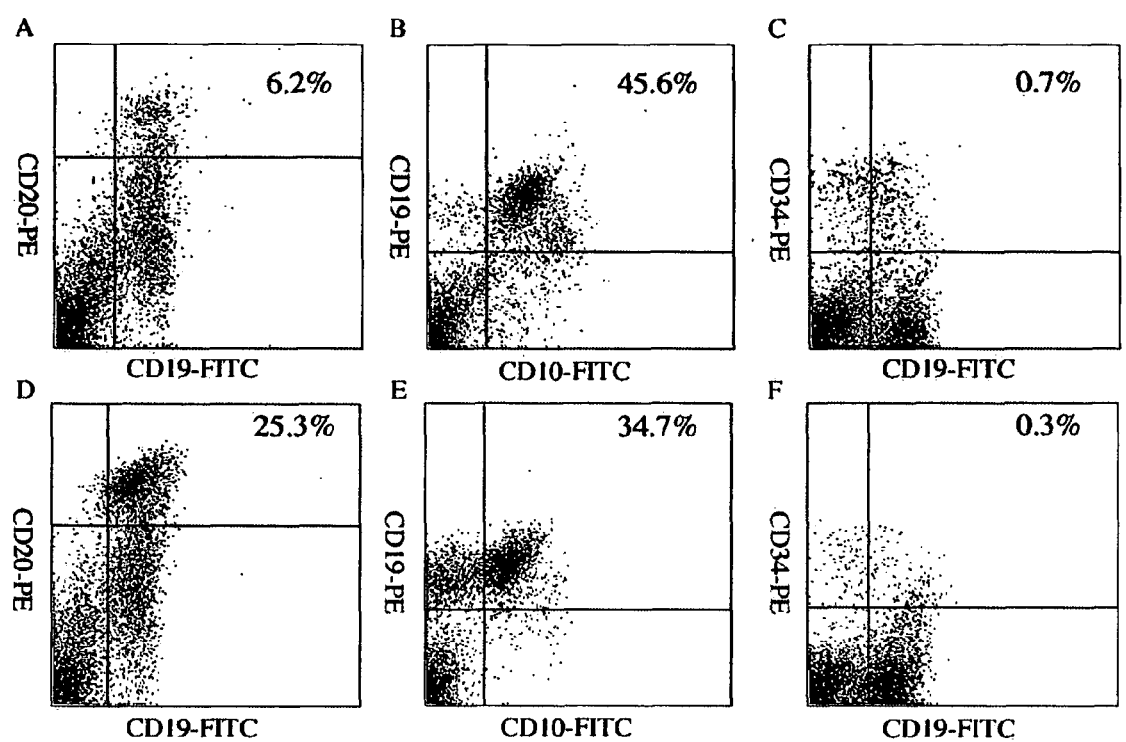
FIG. 6 shows the generation of human B cells in the BM and spleen of NOD/SCID/IL2rg-null mice. A: CD19$^+$ CD20$^{hi}$ mature B cells; B: CD10$^+$CD19$^+$ immature B cells; C: CD34$^+$ CD19$^+$ pro-B cells; D: CD19$^+$CD20$^{hi}$ mature B cells; E: CD10$^+$CD19$^+$ immature B cells; F: CD34$^+$CD19$^+$ pro-B cells.

In Example 6, the presence of human B cells, T cells, and dendritic cells was confirmed in the immune system of the recipient mice (NOD/SCID/IL2R-γc$^{null}$ mice). Cells at each stage of the development of B cells; namely, the presence of CD19$^+$CD20$^{hi}$ mature B cells (FIGS. 6A and 6D), CD10$^+$CD19$^+$ immature B cells (FIGS. 6B and 6E), and CD34$^+$CD19$^+$ pro-B cells (FIGS. 6C and 6F), was confirmed in both the BM (FIGS. 6A to 6C) and the spleen of the engrafted mice (FIGS. 6D to 6F).

Subsequently, the expression of each isotype of human immunoglobulin was examined in human CD19$^+$ cells derived from the BM, peripheral blood (PB), and spleen, 3 months after the transplantation.

Figure 7:
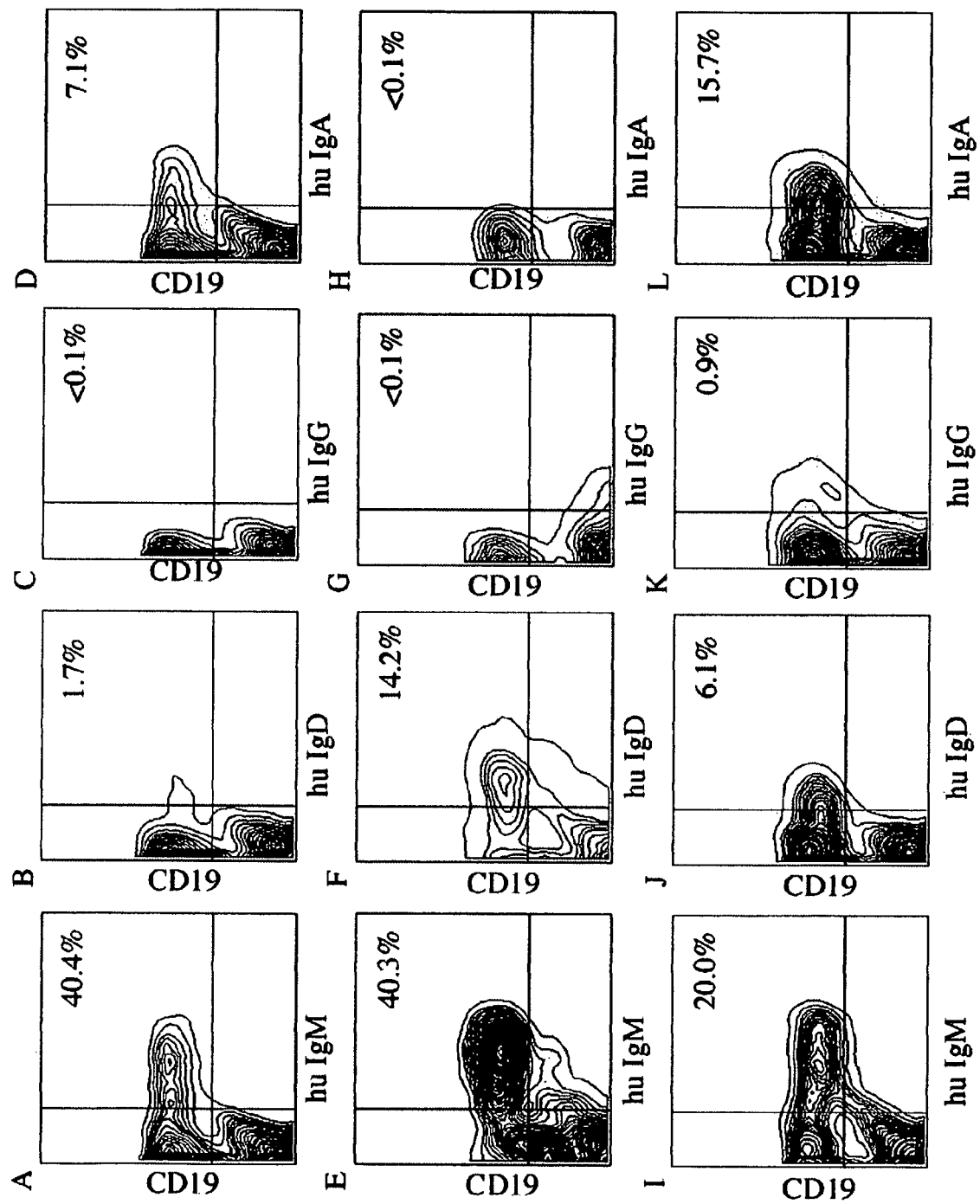
FIG. 7 shows the expression of human immunoglobulins in CD19$^+$ B lineage cells derived from the BM, peripheral blood (PB), and spleen, 3 months after the transplantation. The number in each dot plot represents the ratio (%) of cells, which exhibited positive to both the antibody for each marker representing the origin of the cells and the antibody belonging to each immunoglobulin class. A-D: BM; E-H: PB; I-L: spleen.

The results are shown in FIG. 7. The number in each dot plot represents the ratio (%) of cells, which exhibited positive to both the antibody for each marker representing the origin of the cells and the antibody belonging to each immunoglobulin class. FIG. 7 shows that the expression of immunoglobulin in CD19$^+$ B lineage cells differentiating in lymphoid tissues means that the above lymphoid tissues changed to a human immune system. B precursor cells were maintained and then expressed in the BM, and mature IgM$^+$ and IgD$^+$ B cells were generated in the peripheral blood (PB) (FIG. 7). The presence of human IgA$^+$ B cells in the BM and spleen indicates that a mucosal immune system is reconstructed with human cells.

Subsequently, in order to examine the functions of the aforementioned B cells, the amount of the generated human immunoglobulin contained in the serum of recipients was assayed by the ELISA method. Human CB-derived Lin$^-$CD34$^+$ cells were transplanted into NOD/SCID/β2m$^{null}$ mice and NOD/SCID/IL2rg-null mice. Three months after the transplantation, using such mice, the amounts of human IgM and IgG antibodies generated in the serum thereof were analyzed by ELISA.

As a result, it was found that human IgM (600±197 μg/ml, n=3) and human IgG (256.7±76.4 μg/ml, n=3) were present in the serums of all the recipients examined. Thus, in the present example, it could be confirmed that human immunoglobulin was efficiently generated (Table 3).

TABLE 3

Generation of human IgM and IgG in serums of recipient mice

| Strain | Mouse | IgM (μg/ml) | IgG (μg/ml) |
|---|---|---|---|
| NOD/SCID/IL2rg-null | 1 | 820 | 190 |
| | 2 | 540 | 240 |
| | 3 | 680 | 340 |
| | mean +/− SD | 600 +/− 197 | 256.7 +/− 76.4 |

A significant difference in the generation level of immunoglobulin in the aforementioned engrafted NOD/SCID/β2m$^{null}$ mice and NOD/SCID/IL2rg-null mice was found regarding the amount of a human IgG class antibody in the serums of the recipients. That is to say, this shows that an efficient class switch is controlled by the change to a human immune system in the NOD/SCID/IL2rg-null recipient mice.

Subsequently, the generation of human T cells in a xenogeneic host was analyzed. The generation of human T cells in thymus gland (FIG. 8A) and spleen (FIG. 8B) was analyzed by flow cytometry.

Figure 8:
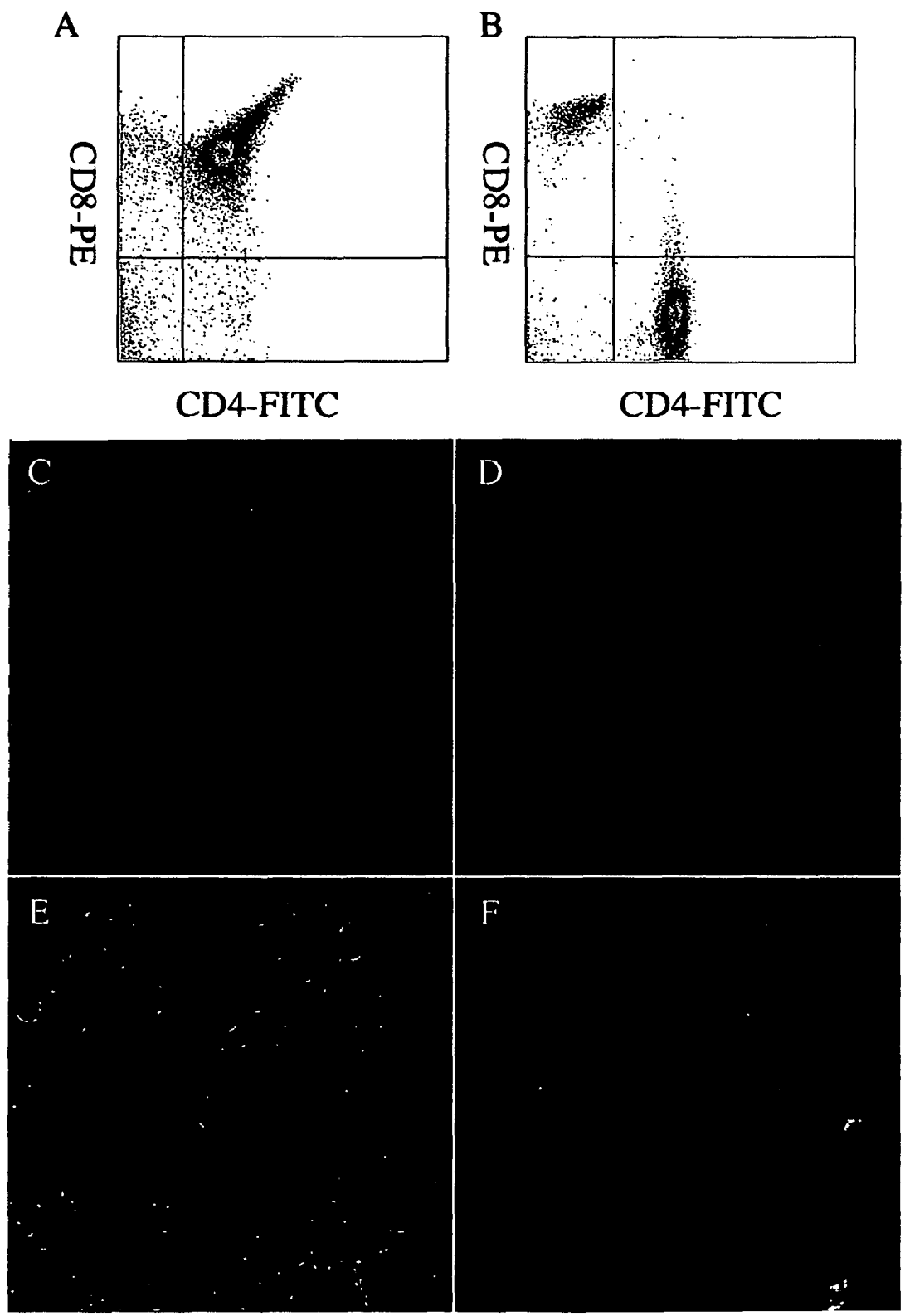
FIG. 8 shows the generation of human T cells in NOD/SCID/IL2rg-null mice. A: thymus gland; B: spleen; C: the T cells in the thymus gland stained with an anti-human CD4 antibody; D: the T cells in the thymus gland stained with an anti-human CD8 antibody; E: a view obtained by overlaying FIG. 8C on FIG. 8D; F: the spleen stained with an anti-human CD4 antibody (green) and an anti-human CD8 antibody (red).

The results are shown in FIG. 8. In the thymus gland, the ratio of immature CD4$^+$CD8$^+$ double positive T cells was found to be 88.1% (A). In contrast, in the spleen as a secondary lymphoid tissue, single positive human T cells such as CD4$^+$CD8$^-$ or CD4$^-$CD8$^+$ made up a major part thereof (B).

Thereafter, the transplanted T cells were identified by an immunofluorescence test. The T cells in the thymus gland were stained with an anti-human CD4 antibody (FIG. 8C) and an anti-human CD8 antibody (FIG. 8D). A section was immobilized with paraformaldehyde, and the section was then treated with a citrate buffer that had been heated. Thereafter, the section was immunostained with the aforementioned antibodies. Detection was carried out using a laser scanning confocal microscope (LSM510Meta: Carl Zeiss). FIG. 8E shows a view obtained by overlaying FIG. 8C on FIG. 8D. This figure shows that a majority of thymocytes were double positive to CD4 and CD8. On the other hand, when the spleen was stained with an anti-human CD4 antibody (green) and an anti-human CD8 antibody (red), it was found that T cells singly positive to CD4 or CD8 were dominant (FIG. 8F).

From the results obtained by immunostaining, it became clear that CD4$^+$CD8$^+$ T cells, CD4$^+$CD8$^-$ T cells, and CD4$^-$CD8$^+$ human T cells form an organized structure in the thymus gland of the recipients. In the secondary lymphoid tissues such as spleen, single positive T cells were present at the CD4/CD8 ratio of 1.39±0.61 (n=5; 0.94-2.43). The above results show that human CB-stem cell-/precursor cell-derived T cells undergo maturation and growth stimuli. This means that the above cells are identical to those existing in living human bodies.

In order that the immune response to antigens optimally changes, it is necessary that dendritic cells or monocytes function as antigen-presenting cells. Thus, the presence of human dendritic cells in the spleen of NOD/SCID/IL2R-γc$^{null}$ mice was analyzed.

Figure 9:
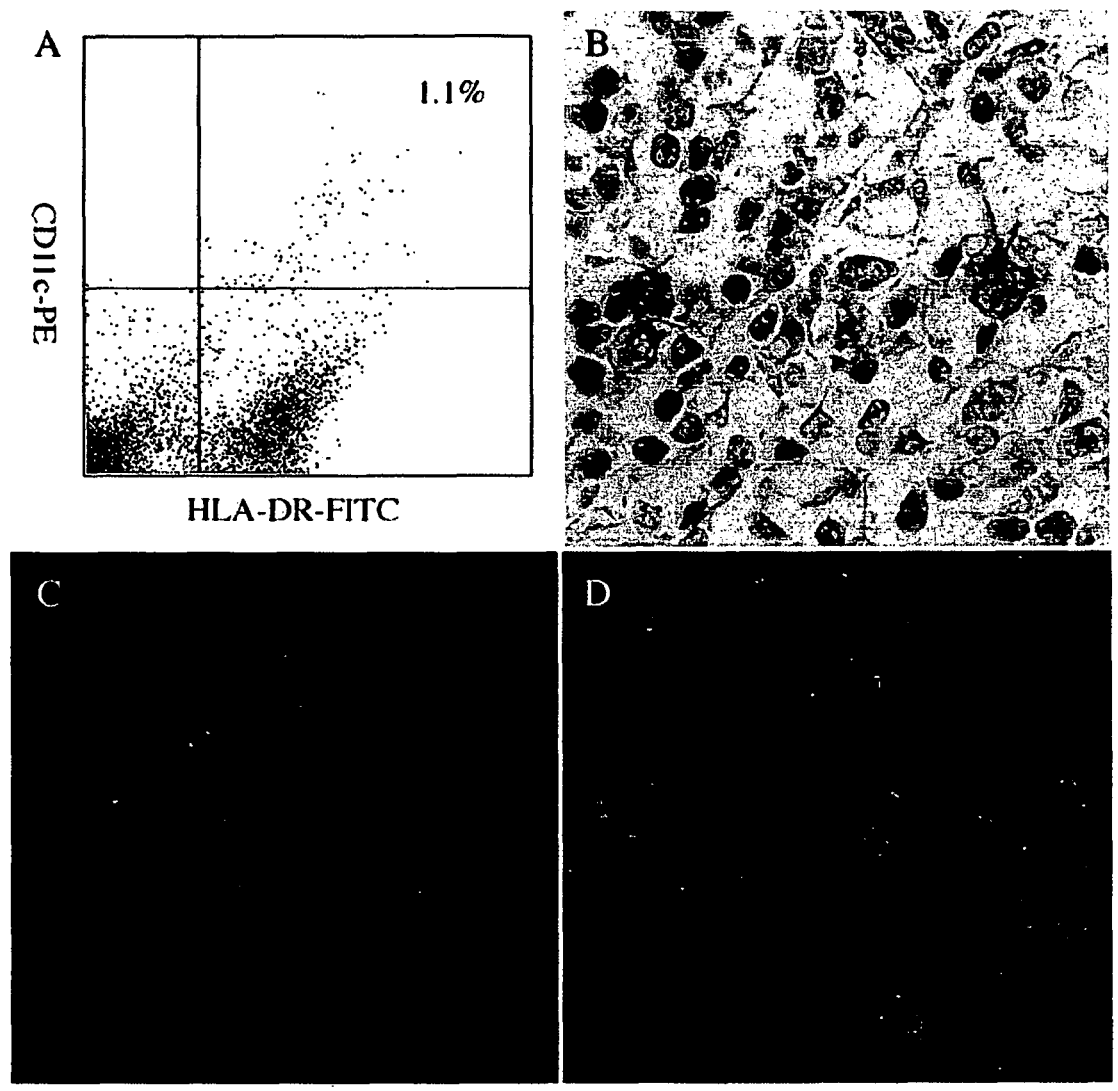
FIG. 9 shows the presence of human dendritic cells in the spleen of NOD/SCID/IL2rg-null mice.

The results are shown in FIG. 9. FIG. 9A shows the presence of HLA$^-$DR$^+$CD11c$^+$ cells in the spleen by flow cytometry. FIG. 9B is a view showing that it was found as a result of immunostaining with an anti-human CD11c antibody that human dendritic cells have estimated morphologic characteristics. FIG. 9A shows that HLA$^-$DR$^+$CD11c$^+$ dendritic cells were present in the spleen of the NOD/SCID/IL2rg-null recipient mice at a frequency of 1.32±0.54% (n=6). In addition, it was also shown as a result of immunostaining with human CD11c that the transplanted human dendritic cells had their morphologic characteristics in the mouse organ (FIG. 9B). The presence of human dendritic cells indicates that structures are formed with human CD19$^+$ cells and CD3$^+$ cells in the spleen of the recipient (FIGS. 9C and 9D), and that as a result, a human immune system is functionally reconstructed in such xenogeneic lymphoid tissues.

These results show that three elements essential for an immune system, namely, human-derived T cells, B cells, and antigen-presenting cells, are differentiated from CB Lin$^-$CD34$^+$ cells at a high rate, with an appropriate maturation of a xenogeneic host (mouse).

Example 8

Reconstruction of Human Mucosal Immunity

Gastrointestinal tract tissues constitute a main site for supporting host protection by mucosal immunity to an extrinsic antigen. The present inventors have confirmed that IgA$^+$ B lineage cells are present in the BM and spleen of a recipient mouse. Thereafter, the inventors have examined that human immunocytes are present in the alimentary canal of a xenogeneic host. An alimentary canal portion ranging from stomach to rectum was extirpated from a mouse, and the portion was then stained with PBS. Thereafter, the portion was immobilized with 3% paraformaldehyde for 1 hour at room temperature. A sample embedded in paraffin was sliced into 5-µm sections, and the sections were then subjected to immunostaining. A laser scanning confocal microscope was used for an immunofluorescence test.

Figure 10:
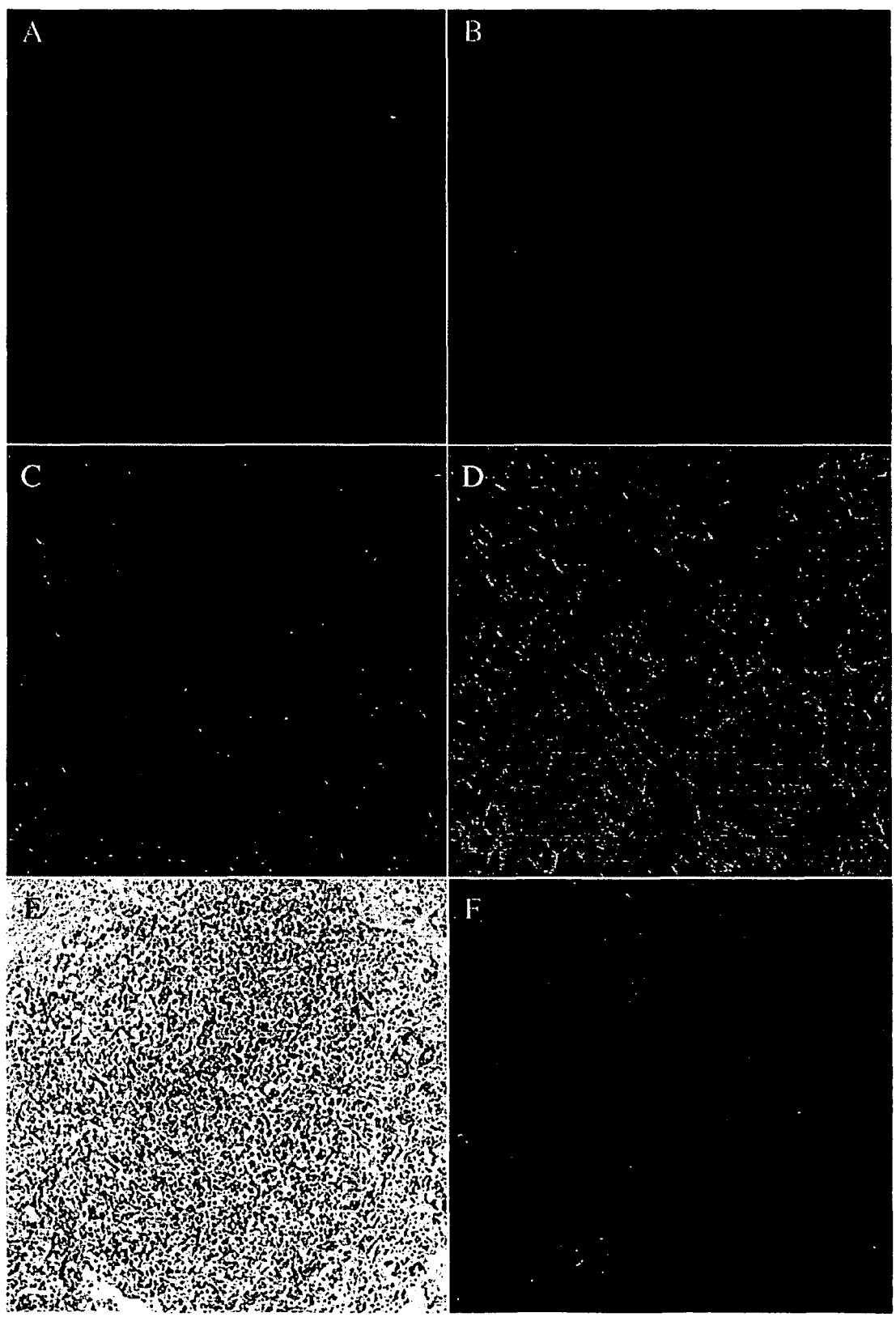
FIG. 10 shows the generation of mucosal immunity in the intestine of NOD/SCID/IL2rg-null mice.

The results are shown in FIG. 10. FIG. 10 shows the generation of mucosal immunity in the alimentary canal of NOD/SCID/IL2rg-null mice. FIGS. 10A and 10B show nuclei stained with DAPI. These figures also show that human mucosal immunity is present in the intestine sample of the recipient mice, as a result of immunostaining with an anti-human CD3 antibody (A, green) and with an anti-human IgA antibody (B, red). FIG. 10C is a view showing the contours of villus obtained by DIC imaging. FIG. 10D is a view obtained by overlaying A, B, and C. As a result of an immunofluorescence test, FIGS. 10A to 10D show that the intestinal villi of the recipient mice contain both human IgA$^+$ B cells and human CD3$^+$ T cells. That is to say, the results show that mucosal immunity was reconstructed with human Lin$^-$CD34$^+$ stem cells/precursor cells. In addition, a nodal structure was observed below the chorion of ileum of an engrafted mouse (FIG. 10E).

The Peyer's patch-like structure is stained with an anti-human IgA antibody (red) and an anti-human CD3 antibody (green). As a result, it was revealed that the subepithelial dome contains a large number of human T cells (FIG. 10F). As stated above, the mouse mesenteric lymph node was also significantly reconstructed with human cells. Accordingly, the model of the present invention is useful as an experimental animal used for analyzing the role of a human mucosal immune system in gastrointestinal tract.

Example 9

Generation of Antigen-Specific Immunoglobulin by Transplanted B Cells

Figure 11:
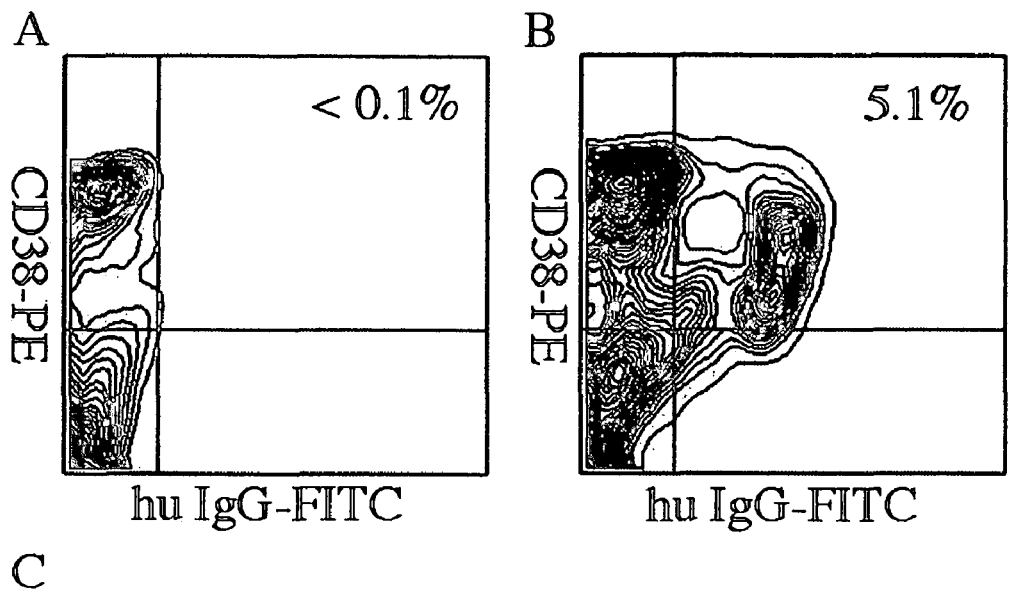
FIG. 11 shows the induction of IgG+ cells following immunization with ovalbumin.
Figure 11:
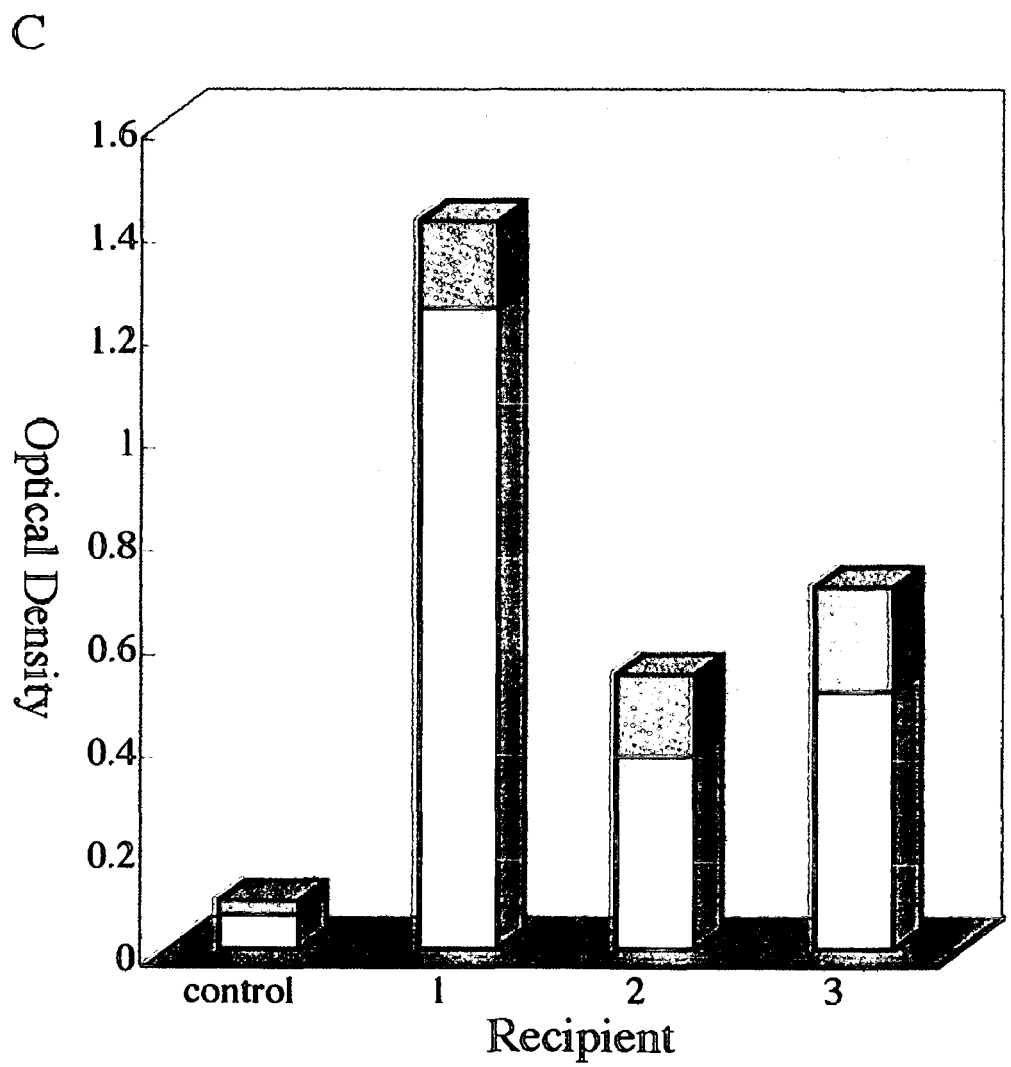

In order to examine the organized response of a human immune system, and also in order to examine the generation of a human antibody specific to an antigen in vivo, three months after the transplantation, three NOD/SCID/IL2rg-null recipient mice were immunized twice with ovalbumin (100 µg, Sigma). Such ovalbumin was emulsified with 100 µg of aluminum hydroxide (Sigma) and then used. After completion of the immunization, the mice were analyzed by flow cytometry. As a result, it was revealed that two weeks after second immunizations, human CD38$^+$IgG$^+$ cells were effectively induced in the BM of the recipient mice (FIG. 11). FIGS. 11A and 11B are views showing the BM cells of the recipient mice analyzed by flow cytometry in terms of the presence of human IgG$^+$ cells, before and after the immunization with ovalbumin.

Thereafter, using the serum of the immunized recipient mice, the generation of human IgM and IgG specific to ovalbumin was measured. The aforementioned three immunized mice, that are, NOD/SCID/IL2rg-null recipient mice, were immunized with ovalbumin. Two weeks after the immunization, the serum was collected from the recipient mice, and the presence of human IgM and IgG specific to ovalbumin was analyzed by the ELISA method. Goat anti-human IgM and IgG antibodies were purchased from Bethyl. After confirming that these antibodies did not involve a cross reaction with mouse anti-human IgM and IgG antibodies, the antibodies were used. As controls for non-specific IgM and IgG, serums derived from NOD/SCID/IL2rg-null recipient mice that had not been immunized were used. In order to analyze ovalbumin-specific human IgM and IgG antibodies, 100 µg/ml ovalbumin was plated at the bottom of a 96-multiwell plate, and it was then used for the ELISA method.

As a result of the ELISA, it was indicated that the optical density of human IgM (white column in FIG. 11C) and that of human IgG (black column in FIG. 11C) in the serum of the immunized recipients (recipient) were extremely higher than those in the serum of non-immunized recipients (control). Moreover, it was also indicated that chimerization of human cells was observed at a high level (FIG. 11). Taking into consideration the fact that ovalbumin is a T-dependent antigen, it is thought that human dendritic cells, T cells, and B cells, which changed to the characteristics of a human immune system, function in harmony to generate antigen-specific human IgM and IgG in xenogeneic host recipient mice.

Example 10

Presence of Alloantigen-Specific Human T Cells

The present example is given to elucidate the alloantigen-specific functions of human T cells, which are differentiated from Lin$^-$CD24$^+$ CB cells in the lymphoid tissues of a xenogeneic host.

Human T cells were isolated from the spleen of a recipient. Thereafter, alloantigen-specific CD4$^+$ T and CD8$^+$ T cell strains were allowed to differentiate. Both the CD4$^+$ T cell strains and CD8$^+$ T cell strains were co-cultured with allogenic target cells (TAK-LCL) to subject to $^{51}$Cr-release assay, so as to examine cytotoxicity to the allogenic target cells.

Various numbers of effector cells and 1×10$^4$ of $^{51}$Cr-labeled allogenic target cells were cultured in 0.2 ml of RPMI1640, to which 10% heat-inactivated fetal bovine serum had been added, in a round bottom microtiter well. Such target cells were also added to a well containing only the medium and a well containing the medium and 1% Triton X-100. The release amounts of $^{51}$Cr in both wells were used as the autonomously released amount of $^{51}$Cr and as the maximum release amount of $^{51}$Cr in the following calculation, respectively. Five hours later, 0.1 ml of supernatant was recovered from each well, and thereafter, a specific $^{51}$Cr release amount was obtained by the following formula:

(Specific $^{51}$Cr release amount) (%)=(actual measurement value (cpm)−autonomous release value (cpm))/(maximum release value) (cpm)−autonomous release value (cpm))×100

In order to determine HLA-restriction, the target cells were pre-incubated with an anti-HLA-A, B, C monoclonal antibody (w6/32)(ATCC) or with an HLA-DR monoclonal antibody (L243)(ATCC) for 30 minutes. Thereafter, the cells were co-cultured with effector T lymphocytes. In each case, cytotoxic assay was carried out at least twice.

KIN-LCL did not share any HLA type with allogenic target cells. Thus, this was used as a negative control (FIG. 12, KIN-LCL, (x)).

The HLA types of effector cells and target cells are as follows: T cells isolated from recipient spleen, HLA-A24/33, B44/52, Cw12/w14, DRB1*1302/*15021, TAK-LCL, HLA-A24/26, B62/−, Cw4/w9, DRB1*0405/*0901, KIN-LCL, HLA-A01/30, B13/17, Cw6/−, DRB1*0701/*0701.

Figure 12:
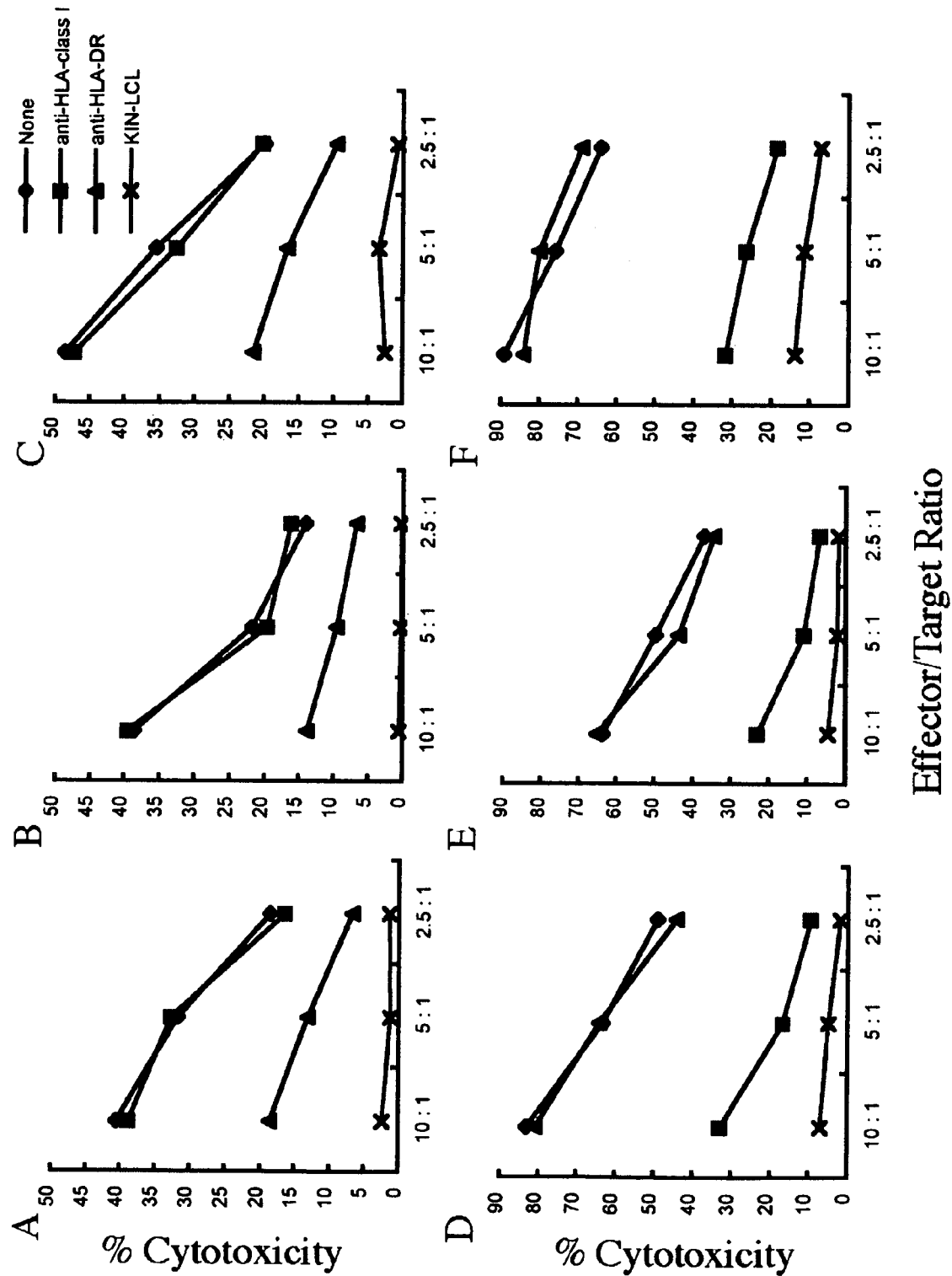
FIG. 12 shows cytotoxicity mediated by human T cells generated in NOD/SCID/IL2rg-null mice to allogenic target cells.

The results are shown in FIG. 12. FIGS. 12A to 12C show the cytotoxicity (% Cytotoxicity) of each of the three CD4$^+$ T cell strains in stimulating cells-concentration depending manner (Effector/Target ratio). The human CD4$^+$ T cell strain was cytotoxic to allogenic LCL (TAK-LCL) used as target cells (FIG. 12, none, (♦)). In order to examine the MHC-restriction of human T cells generated in a xenogeneic environment, an inhibition assay regarding cytotoxicity caused by human T cells was carried out using an anti-HLA class I antibody (anti-HLA class I) and an anti-HLA-DR antibody (anti-HLA-DR). As a result, it was found that the above cytotoxicity was inhibited by the HLA-DR antibody (FIG. 12, anti-HLA-DR, (▲)), but that it was not inhibited by the HLA class I monoclonal antibody (FIG. 12, anti-HLA-class I, (■)). These results show that cytotoxicity is restricted by HLA class II.

FIGS. 12D to 12F show the cytotoxicity of each of the three CD8$^+$ T cell strains in stimulating cells-concentration depending manner. The cytotoxicity caused by CD8$^+$ T was inhibited by the HLA class I monoclonal antibody, but it was not inhibited by the HLA-DR antibody. These results show that cytotoxicity mediated by CD8$^+$ T cells generated in a xenogeneic environment is restricted by the HLA class I antibody, as in the case of cytotoxicity mediated by CD8$^+$ CTL generated in a general environment.

Industrial Applicability

The present invention may provide a method for producing human-derived immunocompetent cells using a newborn immunodeficient animal. Since the newborn immunodeficient animal of the present invention is able to construct a human-derived immune system in the body thereof, it is useful for the functional analysis of lymphoid tissues and the production of a human-derived antibody using B cells.

The invention claimed is:

1. A NOD/SCID/IL2rg-null mouse, which as a newborn had transplanted therein human-derived hematopoietic stem or precursor cells, and which is able to generate immunocompetent cells derived from said human-derived hematopoietic stem or precursor cells and physiologically active substances derived from said immunocompetent cells, and wherein the immunocompetent cells comprise B cells, T cells and dendritic cells, wherein after the mouse has matured for three months: (a) bone marrow tissue extracted from the matured mouse has a ratio of human-derived hematopoietic cells to recipient-derived hematopoietic cells of between 58.8:100 and 90:100, (b) spleen tissue extracted from the matured mouse has a ratio of human-derived antibody-generating cells to recipient-derived antibody-generating cells of between 47.1:100 and 80:100; or (c) peripheral blood extracted from the matured mouse has a ratio of human-derived antibody-generating cells to recipient-derived antibody-generating cells of between 50.1:100 and 80:100.

2. The mouse according to claim 1, wherein the hematopoietic stem or precursor cells are derived from bone marrow, cord blood, or peripheral blood.

3. The mouse according to claim 1, wherein the immunocompetent cells further comprise NK cells and NKT cells.

4. The newborn mouse according to claim 1, wherein the physiologically active substance is a cytokine and/or an immunoglobulin, wherein the immunoglobulin comprises IgG, IgM, IgA and IgD.

5. The mouse according to claim 4, wherein the immunoglobulin further comprises IgE.

6. A method for producing human immunocompetent cells, wherein said method comprises recovering said human immunocompetent cells from the mouse according to claim 1.

7. The mouse according to claim 1, wherein the physiologically active substances are antigen-specific human IgG, IgM, and IgA when the mouse is sensitized to an antigen.

8. The mouse according to claim 7, wherein the amount of the antigen-specific human IgG in the serum of the mouse is 0.1 to 1.0×10$^4$ μg/ml serum.

9. The mouse according to claim 7, wherein the amount of the antigen-specific human IgG in the serum of the mouse is 0.1 to 3.4×10$^3$ μg/ml serum.

10. The mouse according to claim 1, wherein bone marrow tissue extracted from the mouse after it has matured for three months has a ratio of human-derived hematopoietic cells to recipient-derived hematopoietic cells of between 58.8:100 and 90:100.

11. The mouse according to claim 1, wherein spleen tissue extracted from the mouse after it has matured for three months has a ratio of human-derived antibody-generating cells to recipient-derived antibody-generating cells of between 47.1:100 and 80:100.

12. The mouse according to claim 1, wherein peripheral blood extracted from the mouse after it has matured for three months has a ratio of human-derived antibody-generating cells to recipient-derived antibody-generating cells of between 50.1:100 and 80:100.

13. The newborn mouse according to claim 1, wherein after the mouse has matured for three months:
   (a) bone marrow tissue extracted from the matured mouse has a ratio of human-derived hematopoietic cells to recipient-derived hematopoietic cells of between 58.8:100 and 90:100,
   (b) spleen tissue extracted from the matured mouse has a ratio of human-derived antibody-generating cells to recipient-derived antibody-generating cells of between 47.1:100 and 80:100; and
   (c) peripheral blood extracted from the matured mouse has a ratio of human-derived antibody-generating cells to recipient-derived antibody-generating cells of between 50.1:100 and 80:100.

* * * * *